(12) United States Patent
Wanunu et al.

(10) Patent No.: US 11,313,857 B2
(45) Date of Patent: Apr. 26, 2022

(54) SYSTEM AND METHOD FOR IDENTIFYING AND QUANTIFYING SPECIES WITH NANOPORES, USING COMPLEXES OF NANOPARTICLES WITH CARRIER PARTICLES

(71) Applicant: Northeastern University, Boston, MA (US)

(72) Inventors: Meni Wanunu, Needham, MA (US); Mohammadamin Alibakhshi, Boston, MA (US)

(73) Assignee: Northeastern University, Boston, MA (US)

( * ) Notice: Subject to any disclaimer, the term of this patent is extended or adjusted under 35 U.S.C. 154(b) by 234 days.

(21) Appl. No.: 16/376,094

(22) Filed: Apr. 5, 2019

(65) Prior Publication Data

US 2019/0310245 A1  Oct. 10, 2019

Related U.S. Application Data

(60) Provisional application No. 62/654,301, filed on Apr. 6, 2018.

(51) Int. Cl.
*G01N 33/543* (2006.01)
*G01N 27/419* (2006.01)
(Continued)

(52) U.S. Cl.
CPC ..... *G01N 33/54346* (2013.01); *G01N 27/419* (2013.01); *G01N 33/54386* (2013.01);
(Continued)

(58) Field of Classification Search
CPC ....... G01N 33/54306; G01N 33/54353; G01N 33/54393; C07K 16/2863; C07K 16/3007; C40B 40/08; C40B 50/06; C40B 80/00
See application file for complete search history.

(56) References Cited

U.S. PATENT DOCUMENTS 6,863,833 B1   3/2005   Bloom et al.
8,137,569 B2   3/2012   Harnack et al.
(Continued)

FOREIGN PATENT DOCUMENTS

EP   3598133 A1   1/2020
EP   3776080 A    2/2021
(Continued)

OTHER PUBLICATIONS

Hu "Differential Enzyme Flexibility Probed Using Solid-State Nanopores" (ACS Nano 2018 12: 4494-4502). (Year: 2018).*
(Continued)

*Primary Examiner* — Changhwa J Cheu
(74) *Attorney, Agent, or Firm* — Hamilton, Brook, Smith & Reynolds, P.C.

(57) ABSTRACT

A multiplexed digital detection platform embodiment for molecular species in solution is based on a single-molecule immunochemistry, and/or aptamer chemistry, on color-bar-coded beads. Beads that capture molecular species from a complex sample using selective binders are exposed to a test sample, and the captured molecular species is tagged using second affinity probes that are linked to photocleavable nucleic acid particles. In the embodiment, the beads are then introduced to a counter system that comprises a microcavity/nanopore device. Once a bead is captured by the micropore, nucleic acid particles, e.g., reporter nucleic acid nanoparticles (rNANPs), are released using photocleavage, and are detected by the nanopore. Each electrical spike that is uniquely produced by the nucleic acid nanoparticle is counted as a single molecular species, and the total count represents the overall number of molecular species in the sample. Various molecular species can be detected at the same time.

14 Claims, 10 Drawing Sheets
(8 of 10 Drawing Sheet(s) Filed in Color)

(51) Int. Cl.
  *G01N 33/574* (2006.01)
  *G01N 33/566* (2006.01)
(52) U.S. Cl.
  CPC ..... *G01N 33/566* (2013.01); *G01N 33/57434* (2013.01); *G01N 33/57484* (2013.01)

(56) References Cited

U.S. PATENT DOCUMENTS

| | | | |
|---|---|---|---|
| 8,513,165 | B2 | 8/2013 | Takeuchi et al. |
| 8,663,780 | B2 | 3/2014 | Harnack et al. |
| 11,073,764 | B2 | 7/2021 | Wanunu et al. |
| 2003/0169618 | A1 | 9/2003 | Lindsey et al. |
| 2007/0238679 | A1 | 10/2007 | Rank et al. |
| 2009/0214622 | A1 | 8/2009 | Poinern et al. |
| 2011/0263129 | A1 | 10/2011 | Shin et al. |
| 2013/0294972 | A1 | 11/2013 | Kinz-Thompson et al. |
| 2014/0329225 | A1 | 11/2014 | Morin |
| 2015/0090588 | A1 | 4/2015 | Shepard et al. |
| 2016/0062239 | A1 | 3/2016 | Morgan et al. |
| 2016/0200773 | A1 | 7/2016 | Morin |
| 2017/0363741 | A1 | 12/2017 | Send et al. |
| 2018/0043310 | A1 | 2/2018 | Bustamante et al. |
| 2018/0045668 | A1 | 2/2018 | Hyun et al. |
| 2019/0305619 | A1 | 10/2019 | Wanunu |
| 2020/0363406 | A1* | 11/2020 | Chen ................ G01N 33/54346 |
| 2021/0123884 | A1 | 4/2021 | Wanunu et al. |
| 2021/0405533 | A1 | 12/2021 | Wanunu et al. |

FOREIGN PATENT DOCUMENTS

| | | | |
|---|---|---|---|
| GB | | 1337626 A | 11/1973 |
| WO | WO 2016/133570 A1 | | 8/2016 |
| WO | | 2016/161402 A1 | 10/2016 |
| WO | WO 2019/191490 A1 | | 10/2019 |
| WO | WO 2021/062306 A1 | | 4/2021 |

OTHER PUBLICATIONS

Henley "Osmium-Based Pyrimidine Contrast Tags for Enhanced Nanopore-Based DNA Base Discrimination" (PlosONE 2015 Total 12 pages). (Year: 2015).*
Ivankin "Labeled-Free Optical Detection of Biomolecular Translocation Through Nanopore Arrays" (ACS Nano 2014 8: 10774-10781). (Year: 2014).*
Alibakhshi "Picomolar Fingerprinting of Nucleic Acid Nanoparticles Using Solid-State Nanopores" (ACS Nano 2017 11: 9701-9710). (Year: 2017).*
Rudenko et al., "Planar electro-optofluidic chip: Integration of nanopore with optofluidics", Conference on Lasers and Electro-Optics (CLEO) and Quantum Electronics and Laser Science Conference (QELS), May 16-21, 2010, pp. 1-2.
Turkan Yigitbasi (2012). Multiplex Immunoassay and Bead Based Multiplex, Trends in Immunolabelled and Related Techniques, Dr. Eltayb Abuelzein (Ed.), ISBN: 978-953-51-0570-1, InTech, Available from: http://www.intechopen.com/books/trends-in-immunolabelled-and-related-techniques/bead-based-multiplex.
Extended European Search Report for EP Application No. 19167700. 4, entitled "System and Method for Identifying and Quantifying Species with Nanopores, using Complexes of Nanoparticles and Carrier Particles", dated Jan. 7, 2020.
Afonin, K. A, et al., "In Vitro Assembly of Cubic RNA-Based Scaffolds Designed in Silico," Nat. Nanotechnol. 2010, 5, 676-682.
Afonin, K. A, et al., "Specific RNA Self-Assembly with Minimal Paranemic Motifs," J. Am. Chem. Soc. 2008, 130, 93-102.
Afonin, K. A, et al., "Design and Self-Assembly of SiRNA-Functionalized RNA Nanoparticles for Use in Automated Nanomedicine," Nat. Protoc. 2011, 6, 2022-2034.
Afonin, K. A, et al., "Computational and Experimental Characterization of RNA Cubic Nanoscaffolds," Methods 2014, 67, 256-265.
Afonin, K. A, et al., "In Silico Design and Enzymatic Synthesis of Functional RNA Nanoparticles," Acc. Chem. Res. 2014, 47, 1731-1741.
Afonin, K. A, et al., "Engineered RNA Nanodesigns for Applications in RNA Nanotechnology." DNA RNA Nanotechnol. 2013, 1 1-15.
Afonin, K. A, et al., "Multifunctional RNA Nanoparticles," Nano Lett. 2014, 14, 5662-5671.
Akahori et al., "Discrimination of Three Types of Homopolymers in Single-stranded DNA with Solid-state Nanopores through External Control of the DNA Motion," Sci. Rep. 2017, 7, 9073.
Akeson et al., "Microsecond Time-Scale Discrimination Among Polycytidylic Acid, Polyadenylic Acid, and Polyuridylic Acid as Homopolymers or as Segments Within Single RNA Molecules," Biophys. J. 1999, 77, 3227-3233.
Aksimentiev et al., "Microscopic Kinetics of DNA Translocation through Synthetic Nanopores," Biophys. J. 2004, 87, 2086-2097.
An, N., et al., J. Proc Natl Acad Sci USA 2014, 111, (40), 14325-31.
Andersen, H. C., et al., "Rattle: A "Velocity" Version of the Shake Algorithm for Molecular Dynanlics Calculations," J. Comput. Phys. 1983, 52, 24-34.
Andersen, E. S., et al., "Self-Assembly of a Nanoscale DNA Box with a Controllable Lid," Nature 2009, 459, 73-76.
Auernheimer et al., "Photoswitched cell adhesion on surfaces with RGD peptides," J. Am. Chem. Soc. 127, 16107-16110 (2005).
Azagarsamy et al., "Wavelength-controlled photocleavage for the orthogonal and sequential release of multiple proteins," Angew. Chem. Int. Ed. EngL 52, 13803-13807 (2013).
Bacri, L., et al., "Discrimination of Neutral Oligosaccharides through a Nanopore," Biochem. Biophys. Res. Commun. 2011, 412, 561-564.
Baker, C. A, et al., "Photolithographic Fabrication of Microapertures with Well-Defined, Three-Dimensional Geometries for Suspended Lipid Membrane Studies," Anal. Chem., 85: 9078-9086 (2013).
Batcho et al., "Optimized Particle-Mesh Ewald/Multiple-Time Step Integration for Molecular Dynamics Simulations," J. Chem. Phys. 2001, 115, 4003-4018.
Bayley, H., "Nanopore Sequencing: From Imagination to Reality," Clin. Chem. 2015, 61, 25-31.
Bell et al., "Asymmetric Dynamics of DNA Entering and Exiting a Strongly Confining Nanopore," Nat. Commun. 2017, 8, 380.
Best et al., "Optimization of the Additive CHARMM All-Atom Protein Force Field Targeting Improved Sampling of the Backbone $\phi$, $\psi$, and Side-Chain X1 and X2 Dihedral Angles," J. Chem. Theory Comput. 2012, 8, 3257-3273.
Bhagawati, M., et al., "Native laser lithography of His-tagged proteins by uncaging of multivalent chelators," J. Am. Chem. Soc. 132, 5932-5933 (2010).
Bhatia, D., et al., "Icosahedral DNA Nanocapsules by Modular Assembly," Angew. Chem., Int. Ed. 2009, 48, 4134-4137.
Bhatia, D., et al., "Quantum Dot-Loaded Monofunctionalized DNA Icosahedra for Single-Particle Tracking of Endocytic Pathways," Nat. Nanotechnol. 2016, 11, 1112-1119.
Bluemmel, J., et al., "Protein repellent properties of covalently attached PEG coatings on nanostructured SiO(2)-based interfaces,". Biomaterials 28, 4739-4747 (2007).
Boekhoven, J., et al., "Dynamic display of bioactivity through host-guest chemistry," Angew. Chem. Int. Ed. EngL 52, 12077-12080 (2013).
Branton, D., et al., "The Potential and Challenges of Nanopore Sequencing," Nat. Biotechnol. 2008, 26, 1146-1153.
Brieke, C., et al., "Lightcontrolled tools," Angew. Chem. Int. Ed. EngL 51, 8446-8476 (2012).
Bui, et al., "Versatile RNA Tetra-U Helix Linking Motif as a Toolkit for Nucleic Acid Nanotechnology," Nanomedicine 2017, 13, 1137-1146.
Bujold, K E., et al.,"Optimized DNA "Nanu Suitcases" for Encapsulation aml Cumlitiunal Release of SiRNA," J. Am. Chem. Soc. 2016, 138, 14030-14038.
Burden, D. L. et al, "Mechanically Enhancing Planar Lipid Bilayers with a Minimal Actin Cortex," Langmuir, 34: 10847-10855 (2018).

(56) References Cited

OTHER PUBLICATIONS

Cai et al, "Resistive-Pulse Measurements with Nanopipettes: Detection of Vascular Endothelial Growth Factor C (Vegf-C) Using Antibody-Decorated Nanoparticles," Anal. Chem. 2015, 87, 6403-6410.

Cao, C., et al., "Mapping the sensing spots of aerolysin for single oligonucleotides analysis," Nature Communications, 9(2823): 1-9 (2018).

Carson et al., "Smooth DNA Transport through a Narrowed Pore Geometry," Biophys. J. 2014, 107, 2381-2393.

Carson, S., et al., "Challenges in DNA Motion Control and Sequence Readout Using Nanopore Devices," Nanotechnology 2015, 26, 074004.

Cassinelli, V., et al., "One-Step Formation of "Chain-Armor"—Stabilized DNA Nanostructures," Angew. Chem., Int. Ed. 2015, 54, 7795-7798.

Chidchob, P., et al., "Synergy of Two Assembly Languages in DNA Nanostructures: Self-Assembly of Sequence-Defined Polymers on DNA Cages," J. Am. Chem. Soc. 2016, 138, 4416-4425.

Clarke, J., et al., "Continuous base identification for single-molecule nanopore DNA sequencing," Nature Nanotechnology, 4: 265-270 (2009).

Comer et al., "Microscopic Mechanics of Hairpin DNA Translocation through Synthetic Nanopores," Biophys. J. 2009, 96, 593-608.

Cruz-Chu et al., "Water-Silica Force Field for Simulating Nanodevices," J. Phys. Chem. B 2006, 110, 21497-21508.

Cui et al., "Light-triggered multifunctionality at surfaces mediated by photolabile protecting groups," Macromol. Rapid Commun. 34, 310-329 (2013).

Daedalus, "DNA Origami Sequence Design Algorithm for User-defined Structures," 2018, 2 pages.

Darden et al., "Particle Mesh Ewald: An N• Log (N) Method for Ewald Sums in Large Systems," J. Chem. Phys. 1993, 98, 10089-10092.

Dao, et al., "Triggering RNAi with Multifunctional RNA Nanoparticles and Their Delivery," DNA RNA Nanotechnol. 2015, 1, 27-38.

Dekker, C., "Solid-State Nanopores," Nat. Nanotechnol. 2007, 2, 209-215.

Derrington et al., "Nanopore DNA Sequencing with MspA," Proc. Natl. Acad. Sci. U.S.A. 2010, 107, 16060-16065.

Deshpande et al. "Optical Properties of Silicon Nitride Films Deposited by Hot Filament Chemical Vapor Deposition," J. Appl. Phys. 1995, 77, 6534-6541.

Dibrov, et al., "Self-Assembling RNA Square," Proc. Natl. Acad. Sci. U.S.A. 2011, 108, 6405-6408.

Ding, Y., et al., "Internal vs Fishhook Hairpin DNA: Unzipping Locations and Mechanisms in the a-Hemolysin Nanopore," J Phys. Chem. B, 118: 12873-12882 (2014).

Fahie, M., et al., "Resolved Single-Molecule Detection of Individual Species within a Mixture of anti-Biotin Antibodies Using an Engineered Monomeric Nanopore," ASC NANO, 9(2): 1089-1098 (2015).

Fennouri, A, et al., "Single Molecule Detection of Glycosaminoglycan Hyaluronic Acid Oligosacchatides and Depolymerization Enzyme Activity Using a Protein Nanopore," ACS Nano 2012, 6, 9672-9678.

Fleming, A M., et al., "Oxidative DNA damage is epigenetic by regulating gene transcription via base excision repair," Proc. Natl. Acad Sci. USA, 114(10): 2604-2609 (2017).

Fologea et al., "DNA Conformation and Base Number Simultaneously Determined in a Nanopore," Electrophoresis 2007, 28, 3186-3192.

Fologea, D., et al., "Electrical Characterization of Protein Molecules by a Solid-State Nanopore," Appl. Phys. Lett. 2007, 91, 053901.

Fournier et al., "The Solubility of Amorphous Silica at High Temperatures and High Pressures," Am. Mineral. 1977, 62, 1052-1056.

Firnkes, M., et al., "Electrically Facilitated Translocations of Proteins through Silicon Nitride Nanopores: Conjoint and Competitive Action of Diffusion, Electrophoresis and Electroosmosis," Nano Lett. 2010, 10, 2162-2167.

Fuller, C. W., et al., "Real-time single-molecule electronic DNA sequencing by synthesis using polymer-tagged nucleotides on a nanopore array," Proc. Natl. Acad. Sci. USA, 113(19): 5233-5238 (2016).

Gershow et al., "Recapturing and Trapping Single Molecules with a Solid-State Nanopore," Nat. Nanotechnol. 2007, 2, 775-779.

Gilboa et al., "Optically-Monitored Nanopore Fabrication Using a Focused Laser Beam", Sci. Rep. 2018, 8, 9765.

Giorgis et al, "Optical Absorption and Photoluminescence Properties of a-Si1-xNx: H Films Deposited by Plasma-enhanced CVD," Phys. Rev. B: Condens. Matter Mater. Phys. 2000, 61, 4693-4698.

Graf et al., "Fabrication and practical applications of molybdenum disulfide nanopores," Nature Protocols, Nature Publishing Group, GB, vol. 14, No. 4, Mar. 22, 2019, pp. 1130-1168.

Goodman, R.P., et al., "Rapid Chiral Assembly of Rigid DNA Building Blocks for Molecular Nanofabrication," Science 2005, 310, 1661-1665.

Gopfrich, K., et al., "Large-Conductance Transmembrane Porin Made from DNA Origami," ACS Nano, 10: 8207-8214 (2016).

Grabow, et al., "Self-Assembling RNA Nanorings Based on RNAi/Ii Inverse Kissing Complexes," Nano Lett., 2011 11 878-887.

Gropeanu, M., et al., "A versatile toolbox for multiplexed protein micropatterning by laser lithography,". Small 9, 838-845 (2013).

Grunwald, C., et al., "From the Cover: In situ assembly of macromolecular complexes triggered by light," Proc. Natl Acad. Sci. USA 107, 6146-6151 (2010).

Guo, P., et al., "Construction of Folate-Conjugated pRNA of Bacteriophage Phi29 DNA Packaging Motor for Delivery of Chimeric SiRNA to Nasopharyngeal Carcinoma Cells," Gene Ther. 2006, 13, 1553.

Guo, S., et al., "Specific Delivery of Therapeutic RNAs to Cancer Cells Via the Dimerization Mechanism of Phi29 Motor pRNA," Hum. Gene Ther. 2005, 16, 1097-1109.

Guo, P., "The Emerging Field of RNA Nanotechnology," Nat. Nanotechnol. 2010, S, 833-842.

Guo, P., et al., "Uniqueness, Advantages, Challenges, Solutions, and Perspectives in Therapeutics Applying RNA Nanotechnology," Nucleic Acid Ther. 2012, 22, 226-245.

Guo, P., et al., "Inter-RNA Interaction of Phage phi29 pRNA to Form a Hexameric Complex for Viral DNA Transportation," Mol. Cell 1998, 2, 149-155.

Halman, J. R, et al., "Functionally-Interdependent Shape-Switching Nanoparticles with Controllable Properties," Nucleic Acids Res. 2017, 45, 2210-2220.

Han, D., et al., "Single-molecule spectroelectrochemical cross-correlation during redox cycling in recessed dual ring electrode zero-mode waveguides," Chemical science 2017, 8 (8), 5345-5355.

Han, D., et al., "Redox cycling in nanopore-confined recessed dual-ring electrode arrays," The Journal of Physical Chemistry C 2016, 120 (37), 20634-20641.

Harrington, L., et al., "Pim Kinase Inhibitors Evaluated with a Single-Molecule Engineered Nanopore Sensor," Angew. Chem., 127: 8272-8277 (2015).

Harrington, L., et al., "Single-Molecule Protein Phosphorylation and Dephosphorylation by Nanopore Enzymology," ACS Nano, 13: 633-641 (2018).

Haque, F., et al.,"Solid-State and Biological Nanopore for Real-Time Sensing of Single Chemical and Sequencing of DNA," Nano Today 2013, 8, 56-74.

He Y, et al., "Hierarchical Self-Assembly of DNA into Symmetric Supramolecular Polyhedra," Nature 2008, 452, 198-202.

Heng, et al., "Stretching DNA Using the Electric Field in a Synthetic Nanopore," Nano Lett. 2005, 5, 1883-1888.

Henrickson et al, "Driven DNA Transport into an Asymmetric Nanometer-Scale Pore," Phys. Rev. Lett. 2000, 85, 3057-3060.

Hernandez-Ainsa, S. and Keyser, U.F., "DNA origami nanopores: developments, challenges and perspectives," Royal Soc. Chem. Nanoscale, pp. 1-12 (2014).

(56) References Cited

OTHER PUBLICATIONS

Hirano-Iwata, A., et al., "Free-Standing Lipid Bilayers in Silicon Chips-Membrane Stabilization Based on Microfabricated Apertures with a Nanometer-Scale Smoothness," Langmuir, 26(3): 1949-1952 (2010).
Hofmeister et al., "Patterned polymer matrix promotes stemness and cell-cell interaction of adult stem cells", Journal of Biological Engineering, Biomed Central Ltd, vol. 9, article 18, Oct. 12, 2015 Oct. 12, 2015), pp. 1-9.
Holden et al., "Electrical Signature of the Deformation and Dehydration of Microgels During Translocation through Nanopores," Soft Matter 2011, 7, 8035-8040.
Holden et al., "Resistive Pulse Analysis of Microgel Deformation During Nanopore Translocation," J. Phys. Chem. C 2011, 115, 2999-3004.
Howorka, et al., "Nanopore Analytics: Sensing of Single Molecules," Chem. Soc. Rev. 2009, 38, 2360-2384.
Huang, G., et al., "FraC nanopores with adjustable diameter identify the mass of opposite-charge peptides with 44 dalton resolution," Nature Communications, 10(835): 1-10 (2019).
Huang et al., "Large-Area Synthesis of Highly Crystalline WSe2 Monolayers and Device Applications," ACS Nano, vol. 8, No. 1, Jan. 28, 2014, pp. 923-930.
Jadhav, V.; et al., "Porous Zero-Mode Waveguides for Picogram-Level DNA Capture," Nano letters 2018, 19 (2), 921-929.
Jeon, T. J., et al., "Black lipid membranes stabilized through substrate conjugation to a Hydrogel," J Biointerphases, 3(2): FA96-FA100 (2008).
Jeon, T. J., et al., "Hydrogel-Encapsulated Lipid Membranes," J Am. Chem. Soc., 128: 42-43 (2006).
Ji, Z., et al., "Nano-channel of Viral DNA Packaging Motor as Single Pore to Differentiate Peptides with Single Amino Acid Difference," Biomaterials, 182: 227-233 (2018). (From Biomaterials, Author Manuscript; available in PMC, pp. 1-14 (2019)).
Jin, Q., et al., "Unzipping Kinetics of Duplex DNA Containing Oxidized Lesions in an a-Hemolysin Nanopore," J Am. Chem. Soc., 134: 11006-11011 (2012).
Kalsi, S., et al., "Shaped Apertures in Photoresist Films Enhance the Lifetime and Mechanical Stability of Suspended Lipid Bilayers," Biophysical J, 106(8): 1650-1659 (2014).
Kaneko, S., et al., "Photocontrol of cell adhesion on amino-bearing surfaces by reversible conjugation of poly(ethylene glycol) via a photocleavable linker," Phys. Chem. Chem. Phys. 13, 4051-4059 (2011).
Kang, X. F., et al., "A Storable Encapsulated Bilayer Chip Containing a Single Protein Nanopore," J Am. Chem. Soc., 129: 4701-4705 (2007).
Kasianowicz, et al., "Nanoscopic Porous Sensors," Amw. Rev. Anal. Chem. 2008, 1, 737-766.
Keyser et al., "Nanopore Tomography of a Laser Focus," Nano Lett. 2005, 5, 2253-2256.
Kim, M. J., et al., "Characteristics of Solid-State Nanometre Pores Fabricated Using a Transmission Electron Microscope," Nanotechnology 2007, 18, 205302.
Kim, J., et al., "Mimicking dynamic in vivo environments with stimuli-responsive materials for cell culture," Trends Biotechnol. 30, 426-439 (2012).
Kim et al., "Generation of SiRNA Nanosheets for Efficient RNA Interference," Sci. Rep. 2016, 6, 25146.
Kim, M. J., et al., "Rapid Fabrication of Uniformly Sized Nanopores and Nanopore Arrays for Parallel DNA Analysis," Adv. Mater. 2006, 18, 3149-3153.
Klan, P., et al., "Photoremovable protecting groups in chemistry and biology: reaction mechanisms and efficacy," Chem. Rev. 113, 119-191 (2013).
Kloxin., et al., "Photodegradable hydrogels for dynamic tuning of physical and chemical properties," Science 324, 59-63 (2009).
Kloxin., et al., "Tunable hydrogels for external manipulation of cellular microenvironments through controlled photodegradation," Adv. Mater. 22, 61-66 (2010).

Korlach, J, et al., "Selective aluminum passivation for targeted immobilization of single DNA polymerase molecules in zero-mode waveguide nanostructures," Proc Natl Acad Sci U S A 2008, 105 (4), 1176-1181.
Kowal, J., et al., "Hybrid Polymer-Lipid Films as Platforms for Directed Membrane Protein Insertion," Langmuir, 31: 4868-4877 (2015).
Kowalczyk et al, "Modeling the Conductance and DNA Blockade of Solid-state Nanopores," Nanotechnology 2011, 22, 315101.
Kumar, M., et al., "High-Density Reconstitution of Functional Water Channels into Vesicular and Planar Block Copolymer Membranes," J Am. Chem. Soc., 134: 18631-18637 (2012).
Laboria, N., et al., "Control of nanomolar interaction and in situ assembly of proteins in four dimensions by light," Angew. Chem. Int. Ed. EngL 52, 848-853 (2013).
Lamb et al., "Redox-switchable surface for controlling peptide structure," J. Am. Chem. Soc. 133, 8870-8873 (2011).
Langecker, M., et.al., "Nanopores Suggest a Negligible Influence of CpG Methylation on Nucleosome Packaging and Stability," Nano Lett., 15: 783-790 (2015).
Larkin, J.; et al., "High-Bandwidth Protein Analysis Using Solid-State Nanopores," Biophys. J. 2014, 106, 696-704.
Larkin, J.; et al., "Reversible positioning of single molecules inside zero-mode waveguides," Nano letters 2014, 14 (10), 6023-6029.
Larkin, J.; et al., "Length-independent DNA packing into nanopore zero-mode waveguides for low-input DNA sequencing," Nature nanotechnology 2017, 12 (12), 1169.
Lee et al., "A Low-Noise Solid-State Nanopore Platform Based on a Highly Insulating Substrate," Sci. Rep. 2015, 4, 7448.
Lee et al., "Light-triggered in vivo activation of adhesive peptides regulates cell adhesion, inflammation and vascularization of biomaterials," Nat. Mater. 14, 352-360 (2015).
Li, H., et al., "Controllable Self-Assembly of RNA Tetrahedrons with Precise Shape and Size for Cancer Targeting," Adv. Mater. 2016, 28, 7501-7507.
Li, J., et al., "Characterization of Protein Unfolding with Solid-State Nanopores," Protein Pept. Lett. 2014, 21, 256-265.
Li, J., et al., "The Distribution of DNA Translocation Tinles in Solid-State Nanopores," J. Phys.: Condens. Matter 2010, 22, 454129.
Lin et al., "Characterization of DNA duplex Unzipping through a Sub-2 nm Solid-state Nanopore," Chem. Commun. 2017, 53, 3539-3542.
Liu et al., "Atomically Thin Molybdenum Disulfide Nanopores with High Sensitivity for DNA Translocation," ACS Nano, vol. 8, No. 3, Feb. 18, 2014, pp. 2504-2511.
Liu, B., et al., "Bilayer lipid membrane (BLM) based ion selective electrodes at the meso-, micro-, and nano-scales," Biosensors and Bioelectronics, 24: 1843-1849 (2009).
Liu, B., et al., "Dynamic presentation of immobilized ligands regulated through biomolecular recognition," J. Am. Chem. Soc. 132, 13630-13632 (2010).
Liu, Z., et al., "Self-Assembly of Responsive Multilayered DNA Nanocages," J. Am. Chem. Soc. 2015, 137, 1730-1733.
Liu, D., et al., "Using azobenzene-embedded self-assembled monolayers to photochemically control cell adhesion reversibly," Angew. Chem. Int. Ed. Engl. 48, 4406-4408 (2009).
Lombardo et al, "Dielectric Breakdown Mechanisms in Gate Oxides," J. Appl. Phys. 2005, 98, 121301.
Maglia, G., et al., "Enhanced translocation of single DNA molecules through a-hemolysin nanopores by manipulation of internal charge," Proc. Natl. Acad. Sci. USA, 105(50): 19720-19725 (2008).
Maglia, G., et al., "Analysis of single nucleic acid molecules with protein Nanopores," Methods• Enzymol, 475, 591-623 (2010). (From Author Manuscript available in PMC, pp. 1-30, (2011)).
Malmstadt, N., et al., "Long-Lived Planar Lipid Bilayer Membranes Anchored to an In Situ Polymerized Hydrogel," J Adv. Mater., 20: 84-89 (2008).
Martin, W. E., et al., "A comparison of single-molecule emission in aluminum and gold zero-mode waveguides," The Journal of Physical Chemistry A 2016, 120 (34), 6719-6727.
Martyna et al., "Constant Pressure Molecular Dynamics Algorithms," J. Chem. Phys. 1994, 101, 4177-4189.

(56) References Cited

OTHER PUBLICATIONS

Mathe, J., et al., "Nanopore Unzipping of Individual DNA Hairpin Molecules," Biophys. J, 87(5): 3205-3212 (2004).
Mathe, J., et al., "Orientation discrimination of single-stranded DNA inside the a-hemolysin membrane channel," Proc. Natl. Acad. Sci. USA, 102(35): 12377-12382 (2005).
Matsuda., et al., "Tissue engineering based on cell sheet technology," Adv. Mat. 19, 3089-3099 (2007).
Mayer, M., et al., "Microfabricated Teflon Membranes for Low-Noise Recordings of Ion Channels in Planar Lipid Bilayers," Biophys. J, 85(4): 2684-26895 (2003).
McPherson et al., "Underlying Physics of the Thermochemical E Model in Describing Low-field Time-dependent Dielectric Breakdown in SiO2 Thin Films," J. Appl. Phys. 1998, 84, 1513-1523.
Meller et al, "Rapid Nanopore Discrimination between Single Polynucleotide Molecules," Proc. Natl. Acad. Sci. U.S.A. 2000, 97, 1079-1084.
Meller, A., et al., "Single molecule measurements of DNA transport through a nanopore," Electrophoresis, 23: 2583-2591 (2002).
MicroPlex Non-Magnetic Microspheres, "Coupled to Protein or Nucleic Acid," 12 pages, retrieved 2018.
Miyamoto et al.., "An Analytical Version of the Shake and Rattle Algorithm for Rigid Water Models," J. Comput. Chem. 1992, 13, 952-962.
Morton, D., et al., "Tailored polymeric membranes for Mycobacterium smegmatis porin A (MspA) based Biosensors," J Mater. Chem. B, 3: 5080-5086 (2015).
Nakane, J., et al., "Evaluation of nanopores as candidates for electronic analyte detection," Electrophoresis, 23: 2592-2601 (2002).
Nakanishi, J., et al., "Photoactivation of a substrate for cell adhesion under standard fluorescence microscopes," J. Am. Chem. Soc. 126, 16314-16315 (2004).
Nardin, C., et al., "Giant Free-Standing ABA Triblock Copolymer Membranes," Langmuir, 16: 7708-7712 (2000).
Nazari, et al., "Femtosecond Photonic Viral Inactivation Probed Using Solid-State Nanopores," Cornell University Library, Jun. 5, 2018.
Ng, C.C.A., et al., "Using an electrical potential to reversibly switch surfaces between two states for dynamically controlling cell adhesion," Angew. Chem. Int. Ed. Engl. 51, 7706-7710 (2012).
Nicoli et al., "DNA Translocations through Solid-State Plasmonic Nanopores," Nano Lett. 2014, 14, 6917-6925.
Nivala, J., et al., "Unfoldase-mediated protein translocation through an α-hemolysin nanopore," Nat. Biotechnol., 31(3): 247-250 (2013).
Noakes, M. T., et al., "Increasing the accuracy of nanopore DNA sequencing using a time-varying cross membrane voltage," Nature Biotechnology, pp. 1-10 (2019).
Ohmuro-Matsuyama, Y., et al., Photocontrolled cell adhesion on a surface functionalized with a caged arginine-glycine-aspartate peptide. Angew. Chem. Int. Ed. Engl. 47, 7527-7529 (2008).
Ohno, H., et al., "Synthetic RNA Protein Complex Shaped Like an Equilateral Triangle," Nat. Nanotechnol. 2011, 6, 116-120.
Osada, E., et al., "Engineering RNA-Protein Complexes with Different Shapes for Imaging and Therapeutic Applications," ACS Nano 2014, 81 8130-8140.
O'Shaughnessy, T. J., et al., "Laser ablation of micropores for formation of artificial planar lipid bilayers," Biomed Microdevices, 9: 863-868 (2007).
Pang, Y.; Shu, Y. et al., "3D Stretchable Arch Ribbon Array Fabricated via Grayscale Lithography," Scientific Reports, 6(28552): 1-8 (2016).
Pant et al., "Etching of Silicon Nitride in CC12F2, CHF3, SiF4, and SF6 Reactive Plasma: A Comparative Study," Plasma Chem. Plasma Process. 1999, 19, 545-563.
Petersen et al., Phototriggering of cell adhesion by caged cyclic RGD peptides. Angew. Chem. Int. Ed. Engl. 47, 3192-3195 (2008).
Pevarnik, M., et al., "Particle Deformation and Concentration Polarization in Electroosmotic Transport of Hydrogels through Pores," ACS Nano 2013, 7, 3720-3728.

Phillips et al., "Scalable Molecular Dynamics with NAMD," J. Comput. Chem. 2005, 26, 1781-1802.
Piguet, F. et al., "Identification of single amino acid differences in uniformly charged homopolymeric peptides with aerolysin nanopore," Nature Communications, 9: 1-13 (2018).
Plesa, C., et al., "Ionic Permeability and Mechanical Properties of DNA Origami Nanoplates on Solid-State Nanopores," ACS Nano 2014, 8, 35-43.
Pud et al: "Self-Aligned Plasmonic Nanopores by Optically Controlled Dielectric Breakdown", NANO Letters, vol. 15, No. 10, Oct. 14, 2015 (Oct. 14, 2015), pp. 7112-7117.
Reineke et al., "Shift of pH-Value During Thermal Treatments in Buffer Solutions and Selected Foods," Int. J. Food Prop. 2011, 14, 870-881.
Reiner, J. E., et al., "Disease Detection and Management Via Single Nanopore-Based Sensors," Chem. Rev. 2012, 112, 6431-6451.
Robertus, J., et al., "Dynamic control over cell adhesive properties using molecular-based surface engineering strategies," Chem. Soc. Rev. 39, 354-378 (2010).
Rodriguez-Larrea, D., et al., "Multistep protein unfolding during nanopore Translocation," Nature Nanotechnology, 8, 288-295 (2013).
Rolli et al., "Switchable adhesive substrates: revealing geometry dependence in collective cell behavior," Biomaterials 33, 2409-2418 (2012).
Rofeh, J., et al., "Microfluidic block copolymer membrane arrays for nanopore DNA sequencing," Appl. Phys. Lett., 114 (213701): 1-6 (2019).
Rosenstein, J., et al., "Integrated Nanopore Sensing Platform with Sub-Microsecond Temporal Resolution," Nat. Methods 2012, 9, 487-492.
Rothemund et al, "Dielectric Breakdown of Reactively Sputtered Silicon Nitride," Thin Solid Films 1973, 15, 199-205.
Saleh et al., "Direct Detection of Antibody-Antigen Binding Using an on-Chip Artificial Pore," Proc. Natl. Acad. Sci. U.S.A., 2003, 100, 820-824.
Salierno et al., "Photo-activatable surfaces for cell migration assays," Advan. Funct. Mater. 23, 5974-5980 (2013).
Schenk, F. C., et al., "Dual-functionalized nanostructured biointerfaces by click chemistry," Langmuir 30, 6897-6905 (2014).
Shasha, C., et al., "Nanopore-Based Conformational Analysis of a Viral RNA Drug Target," ACS Nano, 8:6 A-F (2014), pp. 6425-6430.
Shlyakhtenko et al., "Silatrane-Based Surface Chemistry for Immobilization of DNA, Protein-DNA Complexes and Other Biological Materials," Ultramicroscopy 2003, 97, 279-287.
Shim, J. W. and Gu, L. Q., "Stochastic Sensing on a Modular Chip Containing a Single-Ion Channel," Anal. Chem., 79: 2207-13 (2007).
Squires, A, et al., "Chapter Fourteen-Single-Molecule Characterization of DNA-Protein Interactions Using Nanopore Biosensors," Methods Enzymol. 2017, 582, 353-385.
Staffa et al., "Temperature Dependence of the Etch Rate and Selectivity of Silicon Nitride over Silicon Dioxide in Remote Plasma NF3/Cl2," Appl. Phys. Lett. 1995, 67, 1902-1904.
Stewart et al., "Programmable RNA Microstructures for Coordinated Delivery of SiRNAs," Nanoscale 2016, 8, 17542-17550.
Studer, A, et al., "Integration and recording of a reconstituted voltage-gated sodium channel in planar lipid bilayers," Biosensors and Bioelectronics,, 26: 1924-1928 (2011).
Tadaki, D., et al., "Mechanically stable solvent free lipid bilayers in nano- and micro-tapered apertures for reconstitution of cell-free synthesized hERG channels," Sci. Rep., 7(17736): 1-10 (2017).
Talaga, et al.,, "Single-Molecule Protein Unfolding in Solid-State Nanopores," J. Am. Chem. Soc. 2009, 131, 9287-9297.
Thakur et al., "Real-time measurement of protein-protein interactions at single-molecule resolution using a biological nanopore," Nature Biotechnology, 37(1): 96-104 (2018).
Van Beest et al., "Force Fields for Silicas and Aluminophosphates Based on ab initio Calculations," Phys. Rev. Lett., 1990, 64, 1955-1958.
Venkatesan, B. M., et al., "Nanopore Sensors for Nucleic Acid Analysis," Nat. Nanotechnol. 2011, 6, 615-624.

(56) References Cited

OTHER PUBLICATIONS

Venta et al., "Differentiation of Short, Single-Stranded DNA Homopolymers in Solid-State Nanopores," ACS Nano 2013, 7, 4629-4636.
Vercoutere, W., et al., "Rapid discrimination among individual DNA hairpin molecules at single-nucleotide resolution using an ion channel," Nature Biotechnology, 19: 248-252 (2001).
Waduge, et al., "Direct and Scalable Deposition of Atomically Thin Low-Noise MoS2 Membranes on Apertures," ACS Nano, vol. 9, No. 7, Jan. 1, 2015, pp. 7352-7359.
Waduge, et al., "Nanopore-Based Measurements of Protein Size, Fluctuations, and Conformational Changes," ACS Nano 2017, 11, 5706-5716.
Wang, Y., et al., "Nanopore-based detection of circulating microRNAs in lung cancer patients," Nature Nanotechnology, 6: 668-674 (2011).
Wang, S., et al., "Engineered Nanopore of Phi29 DNA-Packaging Motor for Real-Time Detection of Single Colon Cancer Specific Antibody in Serum," ACS Nano 2013, 7, 9814-9822.
Wang, Y., et al., "Resistive-Pulse Measurements with Nanopipettes: Detection of Au Nanoparticles and Nanoparticle-Bound Anti-Peanut Igy," Chem. Sci. 2013, 4, 655-663.
Wanunu, M., "Nanopores: A Journey Towards DNA Sequencing," Phys. Life Rev. 2012, 9, 125-158.
Wanunu, M., et al., "DNA Translocation Governed by Interactions with Solid-State Nanopores," Biophys. J. 2008, 95, 4716-4725.
Wanunu, M., et al., "Nanopore Analysis of Individual RNA/Antibiotic Complexes," ACS Nano 2011, 5, 9345-9353.
Wanunu, M., et al., "Electrostatic focusing of unlabelled DNA into nanoscale pores using a salt gradient" Nature Nanotechnology, 5: 160-165 (2010).
Wanunu et al., "Rapid Electronic Detection of Probe-specific microRNAs using Thin Nanopore Sensors," Nat. Nanotechnol. 2010, 5, 807-814.
Wegner et al., "Photocleavable linker for the patterning of bioactive molecules," Scientific Reports 5, Article No. 18309 (2015).
Weis et al., "Dynamic cell-adhesive microenvironments and their effect on myogenic differentiation," Acta Biomaterialia 9, 8059-8066 (2013).
Wescoe, Z. L., et al., "Nanopores Discriminate Among Five CS-Cytosine Variants in DNA," J Am. Chem. Soc., pp. 1-14 (2014).
White, R. J., et al., "White, H. S., Single Ion-Channel Recordings Using Glass Nanopore Membranes," J Am. Chem. Soc., 129: 11766-11775 (2007).
Wirkner et al., "Photoactivatable caged cyclic RGD peptide for triggering integrin binding and cell adhesion to surfaces," Chembiochem 12, 2623-2629 (2011).
Wirkner et al., "Triggered cell release from materials using bioadhesive photocleavable linkers," Adv. Mat. 23, 3907-3910 (2011).
Wong, D., et al., "Single molecule measurements of channel proteins incorporated into biomimetic polymer membrances," Nanotechnology, 17: 3710-3717 (2006).
Wu et al., "The Estimation of Field-Dependent Conductance Change of Nanopore by Field-Induced Charge in the Translocations of Aunps-DNA Conjugates," J. Phys. Chem. C 2014, 118, 26825-26835.
Yamazaki et al., "Label-Free Single-Molecule Thermoscopy Using a Laser-Heated Nanopore," Nano Lett. 2017, 17, 7067-7074.
Yamazaki et al., "Photothermally Assisted Thinning of Silicon Nitride Membranes for Ultrathin Asymmetric Nanopores", ACS Nano, 2018, 12, pp. 12472-12481.
Yeo et al., "Dynamic interfaces between cells and surfaces: electroactive substrates that sequentially release and attach cells," J. Am. Chem. Soc. 125, 14994-14995 (2003).
Ying et al., "Formation of Single Nanopores with Diameters of 20-50 nm in Silicon Nitride Membranes Using Laser-Assisted Controlled Breakdown," ACS Nano, 2019, vol. 12, pp. 11458-11470.
Ying et al., "3D Nanopore Shape Control by Current-Stimulus Dielectric Breakdown", Applied Physics Letter 109, 063105. (Year: 2016).
Yingling et al., "Computational Design of an RNA Hexagonal Nanoring and an RNA Nanotube," Nano Lett., 2007, 7, 2328-2334.
Yoo et al., "Competitive Binding of Cations to Duplex DNA Revealed through Molecular Dynamics Simulations," J. Phys. Chem. B 2012, 116, 12946-12954.
Yu, J., et al., "De Novo Design of an RNA Tile That Self-Assembles into a Homo-Octameric Nanoprism," Nat. Commun. 2015, 6, 5724.
Zakharian, E., "Recording of Ion Channel Activity in Planar Lipid Bilayer Experiments," Methods Mol. Biol., 998(8): 109-118 (2013).
Zhang, Z., et al., "Programmable hydrogels for controlled cell catch and release using hybridized aptamers and complementary sequences," J. Am. Chem. Soc. 134, 15716-15719 (2012).
Zhou, S., et al., "Label-free nanopore single-molecule measurement of trypsin activity," ACS Sensors, pp. 1-30 (2016).

* cited by examiner

FIG. 5A
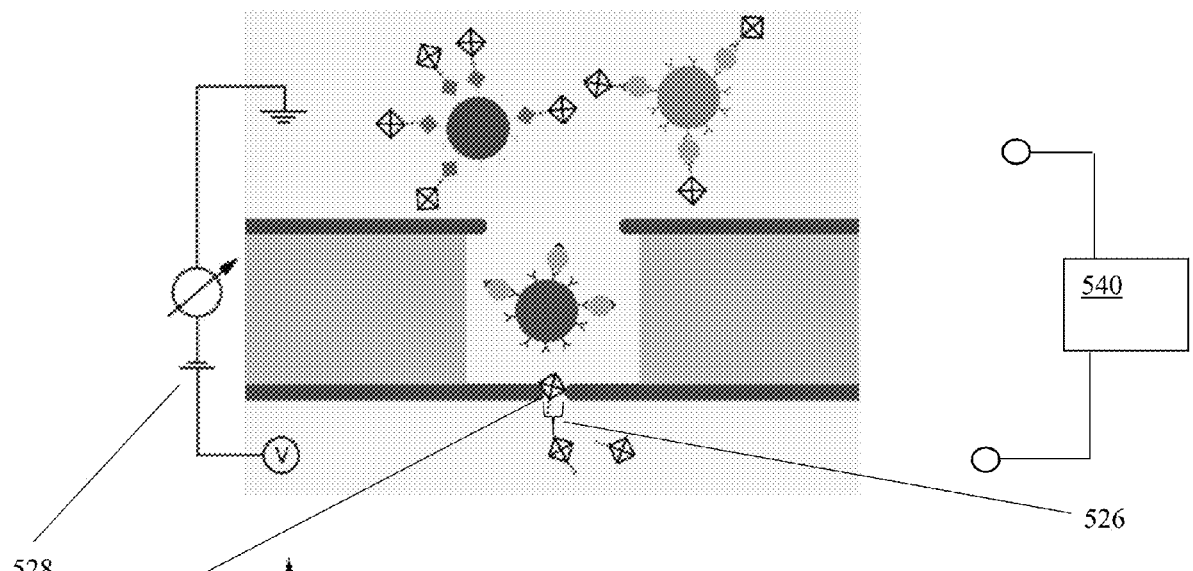
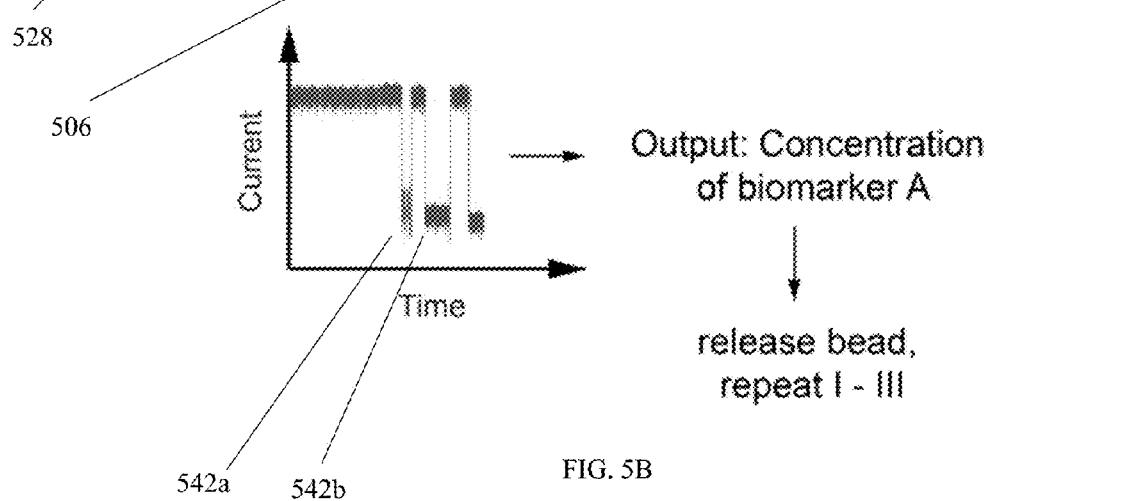
FIG. 5B

SYSTEM AND METHOD FOR IDENTIFYING AND QUANTIFYING SPECIES WITH NANOPORES, USING COMPLEXES OF NANOPARTICLES WITH CARRIER PARTICLES

RELATED APPLICATION

This application claims the benefit of U.S. Provisional Application No. 62/654,301, filed on Apr. 6, 2018. The entire teachings of the above application are incorporated herein by reference.

GOVERNMENT SUPPORT

This invention was made with government support under Grant No. 1R01HG009186 awarded by National Institutes of Health. The government has certain rights in the invention.

BACKGROUND

A major problem plaguing health in society today is a need for rapid tools for accurate diagnosis of disease. Early signs of cancers, infections, and other diseases are typically accompanied by molecular indicators, so called biomarkers, that are often too low in abundance to quantify using conventional techniques. Protein biomarkers are especially difficult to diagnose because they cannot be directly copied to produce multiple copies, and techniques such as the enzyme-linked immunosorbent assay (ELISA) have their limitations in terms of what detection limits can be achieved. For the case of nucleic acid biomarkers, the polymerase chain reaction (PCR) technique is the tool of choice to amplify the target biomarker, although inherent bias during the amplification steps precludes accurate quantification. There is an ongoing need for rapid tools for accurate diagnosis of disease, and to allow early detection of conditions such as cancer diseases and infectious diseases.

SUMMARY

An embodiment according to the invention provides a reliable portable platform that can count a number of molecular species, such as but not limited to biomarkers, in a complex sample. A multiplexed digital detection platform for molecular species in solution is based on a single-molecule immunochemistry, and/or aptamer chemistry, on color-barcoded beads. Beads that capture molecular species from a complex sample using selective aptamers/antibodies are exposed to a test sample (e.g., serum), and after cleanup, the captured molecular species is tagged using second affinity probes (e.g., antibodies, aptamers) that are linked to photocleavable nucleic acid particles. The beads are then introduced to a counter system that comprises a microcavity/nanopore device. Once a bead is captured by the micropore, nucleic acid particles, e.g. reporter nucleic acid nanoparticles (rNANPs), are released using photocleavage, and are detected by the nanopore. Each electrical spike that is uniquely produced by the nucleic acid nanoparticle is counted as a single molecular species, and the total count represents the overall number of molecular species in the sample (e.g., the biomarker count). Various molecular species can be detected at the same time. The device can, for example, allow early detection of cancer diseases and infectious outbreaks.

In accordance with an embodiment according to the invention, there is provided a method of identifying and quantifying a species from a sample. The method comprises capturing a species-loaded complex, the species-loaded complex comprising: (i) the species, isolated from the sample, (ii) a carrier particle, (iii) a first species-specific binder, binding the species to the carrier particle, (iv) a second species-specific binder, bound to the species, (v) a nanoparticle, and (vi) a cleavable linker, linking the second species-specific binder to the nanoparticle. While the species-loaded complex is captured, the method comprises identifying the carrier particle based on its physical characteristics, thereby permitting distinguishing a type of the carrier particle from amongst a plurality of different carrier particle types, each of the plurality of different carrier particle types corresponding uniquely to one of a plurality of different species in the sample. The method further comprises, upon having identified the carrier particle, cleaving the cleavable linker while applying a voltage to an electrolyte surrounding the species-loaded complex, the voltage being sufficient to translocate the nanoparticle through a nanopore; and detecting an electrical current change produced as a result of the translocation of the nanoparticle through the nanopore, thereby permitting quantification of the species.

In further, related embodiments, capturing the species-loaded complex may comprise capturing the species-loaded complex within a microcavity structure defining a microcavity, the species-loaded complex being captured within the microcavity, the microcavity structure defining a first opening of the microcavity comparable in size to the carrier particle, and the microcavity structure defining a second opening of the microcavity that is a nanopore, sized to have a comparable dimension to the nanoparticle and to permit translocation of the nanoparticle. The microcavity may have a diameter of between about 2 microns and about 10 microns. The nanopore may have a diameter of between about 1 nanometer and about 50 nanometers. The nanoparticle may comprise a deformable reporter nucleic acid nanoparticle. Detecting the electrical current change may comprise detecting a temporary reduction in ionic current through the nanopore produced by transient occlusion of the nanopore by the nanoparticle during the translocation of the nanoparticle through the nanopore produced by the applying the voltage. The method may further comprise electrically translating the electrical current change to an electrical signal representing an integer counting of the species. The cleavable linker may comprise at least one of a photocleavable linker and a chemically-cleavable linker. The cleavable linker may comprise a photocleavable linker, and cleaving the cleavable linker may comprise illuminating the photocleavable linker with light of a wavelength specific to cleaving of the photocleavable linker. Identifying the carrier particle based on its physical characteristics may comprise optically discriminating the carrier particle, each of the plurality of different carrier particle types comprising an optical signature corresponding uniquely to one of the plurality of different species in the sample. The carrier particle may comprise a bead having a diameter between about 2 microns and about 10 microns.

In other, related embodiments, at least one of the first species-specific binder and the second species-specific binder may comprise at least one of: a protein, a nucleic acid, a polymer and a chelating agent. At least one of the first species-specific binder and the second species-specific binder may comprise at least one of: deoxyribonucleic acid (DNA), ribonucleic acid (RNA), a polymer, an antibody, an aptamer, a single-stranded nucleic acid, a Clustered Regularly Interspaced Short Palindromic Repeats (CRISPR) nucleic acid guide, and a polyhistidine tag. The first species-specific binder and the second species-specific binder may comprise a pair of antibodies, each of the antibodies binding to different epitopes of the same species. At least one of the first species-specific binder and the second species-specific binder may comprise a linker polymer, wherein the linker polymer is a heteropolymer. The species may comprise at least one of: a nucleic acid molecule, a protein, a cell, a bacteria, a virus, a fungus, a polypeptide, a polysaccharide and an organic drug. The species may comprise at least a portion of at least one of: a biomarker, a circulating tumor cell nucleic acid, a circulating tumor protein, a circulating tumor cell, and a white blood cell. The species may comprise at least one of: a prostate-specific antigen; thrombin; an indicator of metastatic cancer; a fetal nucleic acid; a fetal protein. The sample may be a blood sample. The sample may be a maternal blood sample, and the species may comprise at least one of a fetal nucleic acid and a fetal protein.

In further, related embodiments, the method may further comprise, with a computer processor: following the capturing of the species-loaded complex, controlling an optical component and an electrical signal processing component to identify the carrier particle based on its physical characteristics; following the identification of the carrier particle, controlling a cleaving component to cleave the cleavable linker; and controlling current detection circuitry to detect the electrical current change produced as a result of the translocation of the nanoparticle through the nanopore. The method may comprise performing the method for a plurality of different species in the same sample simultaneously, using a plurality of nanopores. The method may comprise applying the voltage to the electrolyte surrounding the species-loaded complex, using a plurality of electrodes, each electrode of the plurality of electrodes corresponding to a single nanopore. The method may comprise cleaving the cleavable linker using an electrode in electrical connection with the nanopore. The electrode may define at least part of a wall of the nanopore.

In another embodiment according to the invention, there is provided a device to identify and quantify a species from a sample. The device comprises a microcavity structure defining a microcavity, the microcavity structure defining a first opening of the microcavity comparable in size to a carrier particle to capture a species-loaded complex. The species-loaded complex comprises: (i) the species, isolated from the sample, (ii) the carrier particle, (iii) a first species-specific binder, binding the species to the carrier particle, (iv) a second species-specific binder, bound to the species, (v) a nanoparticle, and (vi) a cleavable linker, linking the second species-specific binder to the nanoparticle. The microcavity structure further defines a second opening of the microcavity that is a nanopore, sized to have a comparable dimension to the nanoparticle and to permit translocation of the nanoparticle. A carrier particle detection component is configured to, while the species-loaded complex is captured, identify the carrier particle based on its physical characteristics, thereby permitting distinguishing a type of the carrier particle from amongst a plurality of different carrier particle types, each of the plurality of different carrier particle types corresponding uniquely to one of a plurality of different species in the sample. A voltage source is configured to apply a voltage to an electrolyte surrounding the species-loaded complex, the voltage being sufficient to translocate the nanoparticle through a nanopore. A cleaving component is configured to, upon having identified the carrier particle, cleave the cleavable linker while the voltage is applied to the electrolyte surrounding the species-loaded complex. An electrical current processing circuit is configured to detect an electrical current change produced as a result of the translocation of the nanoparticle through the nanopore, thereby permitting quantification of the species.

In further, related embodiments, the microcavity may have a diameter of between about 2 microns and about 10 microns. The nanopore may have a diameter of between about 1 nanometer and about 50 nanometers. The nanoparticle may comprise a deformable reporter nucleic acid nanoparticle. The electrical current processing circuit may be configured to detect a temporary reduction in ionic current through the nanopore produced by transient occlusion of the nanopore by the nanoparticle during the translocation of the nanoparticle through the nanopore produced by the applying the voltage. The electrical current processing circuit may be further configured to translate electrically the electrical current change to an electrical signal representing an integer counting of the species. The cleavable linker may comprise a photocleavable linker, and the device may further comprise an illumination source to illuminate the photocleavable linker with light of a wavelength specific to cleaving of the photocleavable linker. The carrier particle detection component may be configured to discriminate the carrier particle optically, each of the plurality of different carrier particle types comprising an optical signature corresponding uniquely to one of the plurality of different species in the sample.

In other, related embodiments, the device may further comprise a processor, and a memory with computer code instructions stored thereon. The processor and the memory, with the computer code instructions may be configured to implement: (i) an optical identification control module configured to, following the capturing of the species-loaded complex, control an optical component and an electrical signal processing component to identify the carrier particle based on its physical characteristics; (ii) a cleaving control module configured to, following the identification of the carrier particle, controlling a cleaving component to cleave the cleavable linker; and (iii) an electrical current detection control module configured to control current detection circuitry to detect the electrical current change produced as a result of the translocation of the nanoparticle through the nanopore. The device may comprise a plurality of the microcavity structures, each microcavity structure of the plurality of microcavity structures defining a second opening of each microcavity that is a nanopore, sized to have a comparable dimension to the nanoparticle and to permit translocation of the nanoparticle. The device may comprise a plurality of electrodes, each electrode of the plurality of electrodes corresponding to a single nanopore. The device may comprise an electrode, in electrical connection with the nanopore, configured to cleave the cleavable linker. The electrode may be formed of at least part of the microcavity structure that defines the nanopore of the microcavity.

In another embodiment according to the invention, there is provided a species-loaded complex to permit identification and quantification of a species in a sample. The species-loaded complex comprises (i) the species, isolated from the sample; (ii) a carrier particle; (iii) a first species-specific binder, binding the species to the carrier particle; (iv) a second species-specific binder, bound to the species; (v) a nanoparticle; and (vi) a cleavable linker, linking the second species-specific binder to the nanoparticle.

In further, related embodiment, the nanoparticle may comprise a deformable reporter nucleic acid nanoparticle. The cleavable linker may comprise at least one of a photocleavable linker and a chemically-cleavable linker. The carrier particle may comprise a bead having a diameter between about 2 microns and about 10 microns. At least one of the first species-specific binder and the second species-specific binder may comprise at least one of: a protein, a nucleic acid, a polymer and a chelating agent. At least one of the first species-specific binder and the second species-specific binder may comprise at least one of: deoxyribonucleic acid (DNA), ribonucleic acid (RNA), a polymer, an antibody, an aptamer, a single-stranded nucleic acid, a Clustered Regularly Interspaced Short Palindromic Repeats (CRISPR) nucleic acid guide, and a polyhistidine tag. The first species-specific binder and the second species-specific binder may comprise a pair of antibodies, each of the antibodies binding to different epitopes of the same species. At least one of the first species-specific binder and the second species-specific binder may comprise a linker polymer, wherein the linker polymer is a heteropolymer.

In another embodiment according to the invention, there is provided a kit for identifying and quantifying a species from a sample. The kit comprises a plurality of different carrier particle types, each of the plurality of different carrier particle types corresponding uniquely to one of a plurality of different species in the sample. For each of the plurality of different species in the sample, the kit comprises a first species-specific binder, to specifically bind the species to the carrier particle to which it uniquely corresponds. For each of the plurality of different species in the sample, the kit comprises a nanoparticle complex comprising: (i) a second species-specific binder, to bind specifically to the species, (ii) a nanoparticle, and (iii) a cleavable linker, linking the second species-specific binder to the nanoparticle.

In further, related embodiments, the nanoparticle may comprise a deformable reporter nucleic acid nanoparticle. The cleavable linker may comprise at least one of a photocleavable linker and a chemically-cleavable linker. The carrier particle may comprise a bead having a diameter between about 2 microns and about 10 microns. At least one of the first species-specific binder and the second species-specific binder may comprise at least one of: a protein, a nucleic acid, a polymer and a chelating agent. At least one of the first species-specific binder and the second species-specific binder may comprise at least one of: deoxyribonucleic acid (DNA), ribonucleic acid (RNA), a polymer, an antibody, an aptamer, a single-stranded nucleic acid, a Clustered Regularly Interspaced Short Palindromic Repeats (CRISPR) nucleic acid guide, and a polyhistidine tag. The first species-specific binder and the second species-specific binder may comprise a pair of antibodies, each of the antibodies binding to different epitopes of the same species.

BRIEF DESCRIPTION OF THE DRAWINGS

The patent or application file contains at least one drawing executed in color. Copies of this patent or patent application publication with color drawings will be provided by the Office upon request and payment of the necessary fee.

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 5A is a schematic diagram illustrating nanoparticle counting and quantification, in accordance with an embodiment of the invention.

FIG. 5B is a schematic diagram illustrating recording of ion flux as a function of time, produced by translocation of a nanoparticle through a nanopore, to permit the quantification, in accordance with an embodiment of the invention.

In FIG. 6A, layers are created on a silicon wafer and a pillar is created by e-beam lithography or photolithography; in FIG. 6B, another layer is deposited on the wafer; in FIG. 6C, resist lift-off is performed, a membrane is created and a transmission electron microscope is used to drill a nanopore in the membrane; FIG. 6D is a top view microscope image of the membrane; FIG. 6E is a bottom view image of the membrane; FIG. 6F shows a transmission electron micrograph image of the membrane; and FIG. 6G shows an image of the transmission electron microscope-drilled nanopore.

DETAILED DESCRIPTION

A description of example embodiments follows.

An embodiment according to the invention provides a reliable portable platform that can count a number of molecular species, such as but not limited to biomarkers, in a complex sample. A multiplexed digital detection platform for molecular species in solution is based on a chemistry, e.g., single-molecule immunochemistry, and/or aptamer chemistry, on color-barcoded beads. Beads that capture molecular species from a complex sample using specific binders, e.g., selective aptamers and/or antibodies are exposed to a test sample (e.g., serum), and after cleanup, the captured molecular species is tagged using second affinity probes (e.g., antibodies, aptamers) that are linked to photocleavable nucleic acid particles. The beads are then introduced to a counter system that comprises a microcavity/nanopore device. Once a bead is captured by the micropore, nucleic acid particles, e.g., reporter nucleic acid nanoparticles (rNANPs), are released using photocleavage, and are detected by the nanopore. Each electrical spike that is uniquely produced by the nucleic acid nanoparticle is counted as a single molecular species, and the total count represents the overall number of molecular species in the sample (e.g., the biomarker count). Various molecular species can be detected at the same time. The device can, for example, allow early detection of cancer diseases and infectious outbreaks.

Figure 1:
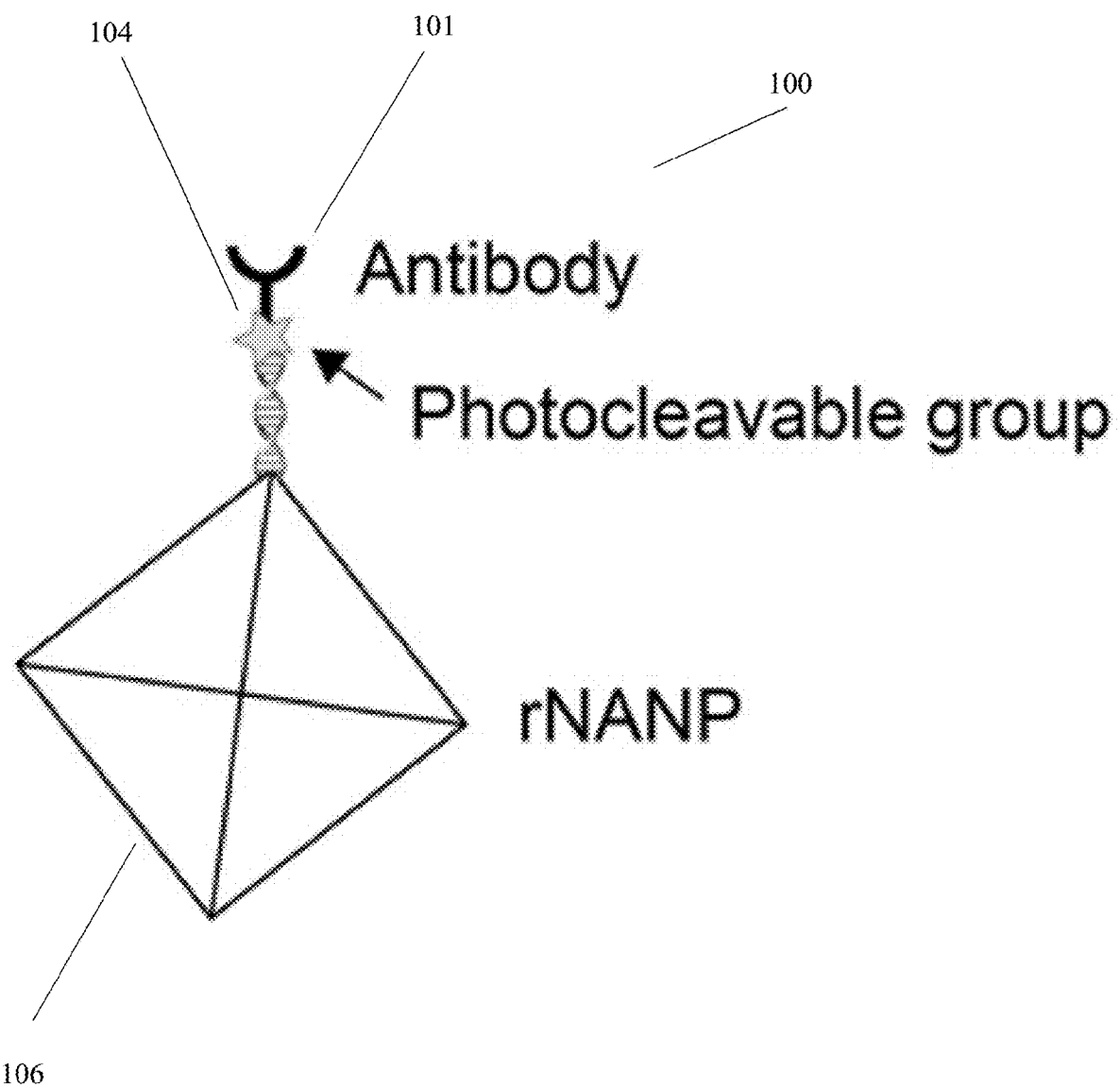
FIG. 1 is a schematic diagram of a portion of a species-loaded complex that is used to identify and quantify a species from a sample, in accordance with an embodiment of the invention.

FIG. 1 is a schematic diagram of a portion of a species-loaded complex that is used to identify and quantify a species from a sample, in accordance with an embodiment of the invention. In the portion 100 of the species-loaded complex that is shown in FIG. 1, a nanoparticle 106, such as a reporter nucleic acid nanoparticle (rNANP), is prepared such that it is linked to a species-specific binder 101, e.g., an antibody, through a cleavable linker, such as a photocleavable group 104. The portion shown in FIG. 1 is combined with other portions of the species-loaded complex, as described further below.

Figure 2:
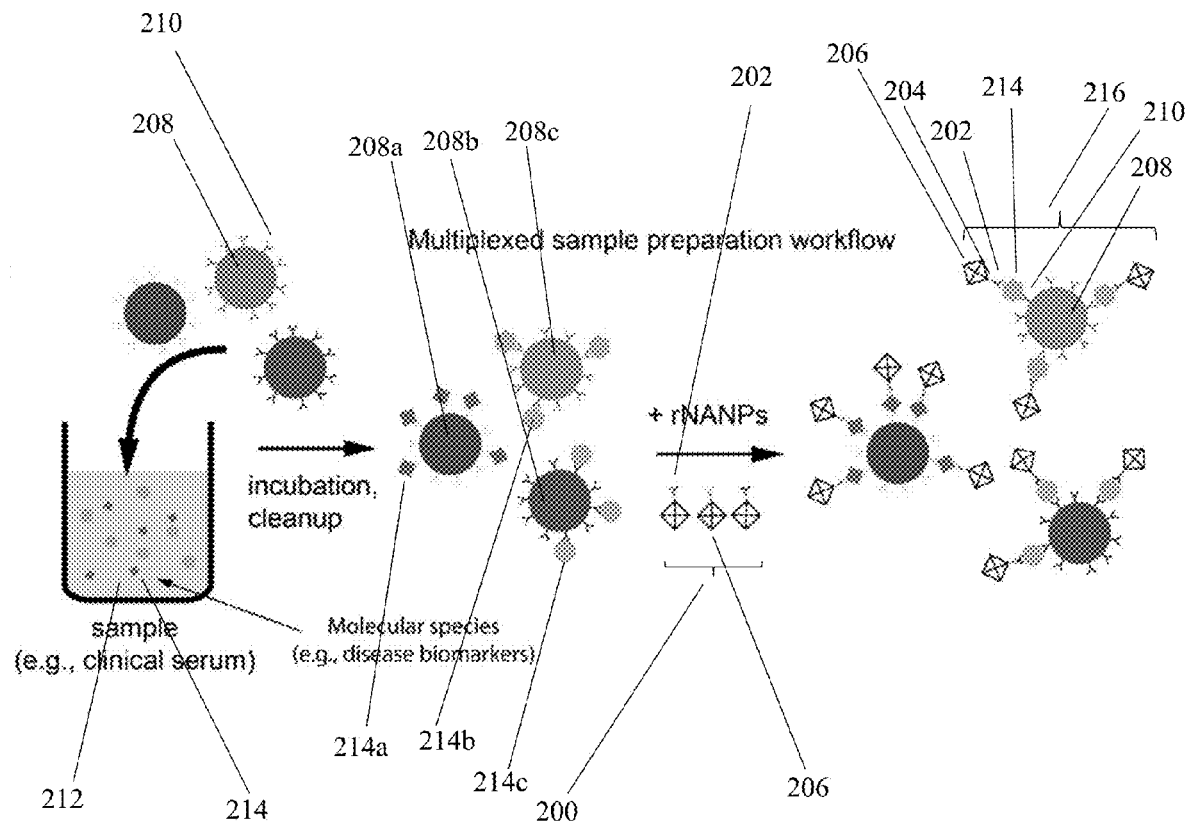
FIG. 2 is a schematic diagram of a multiplexed sample preparation workflow, in accordance with an embodiment of the invention.

FIG. 2 is a schematic diagram of a multiplexed sample preparation workflow, in accordance with an embodiment of the invention. Carrier particles 208, such as beads having a diameter between about 2 microns and about 10 microns, are coated with a different species-specific binder 210 from the species-specific binder 101 of FIG. 1, e.g., a different antibody. Also, multiple different species-specific binders 210 are used, which correspond uniquely to multiple different types of carrier particles 208. For example, the carrier particles can be of different colors, so that the multiple different types of species-specific binder 210 correspond uniquely to one each of the multiple different colors of carrier particles 208. In addition to beads, it will be appreciated that other shapes and types of carrier particles 208 can be used. The carrier particles 208 are incubated with the sample 212 of interest, such as clinical serum, which contains species 214 such as disease biomarkers. As a result of the incubation and the unique correspondence of the species-specific binders 210 with the carrier particles 208, each of the different carrier particle types 208a, 208b, 208c corresponds uniquely to one of the multiple different species 214a, 214b, 214c in the sample. After incubation, the particles are then treated in a cleanup step to remove all unreacted species in the sample. The result is that the species 214 are isolated from the sample 212, and bound to the carrier particles 208 by the species-specific binder 210. Then, the portion 100 of the species-loaded complex that was shown in FIG. 1 is incubated with the particles. In the workflow of FIG. 2, the portion 200 includes nanoparticles 206 (here, rNANPs) that are linked to second species-specific binders 202 that are also specific to each of the species 214 picked up by the beads. Nanoparticles used in accordance with an embodiment of the invention can, for example, be deformable reporter nucleic acid nanoparticles (rNANPs), but can also be other nanoparticles, such as a fragment of DNA or other nucleic acid, or metal nanoparticle coated with an organic, deformable substance. The result of this incubation is a species-loaded complex 216, that includes six components: (i) the species 214, isolated from the sample 212, (ii) the carrier particle 208, (iii) a first species-specific binder 210, binding the species 214 to the carrier particle 208, (iv) a second species-specific binder 202, bound to the species, (v) a nanoparticle 206 (such as an rNANP), and (vi) a cleavable linker 204, linking the second species-specific binder 202 to the nanoparticle 206.

Figure 3:
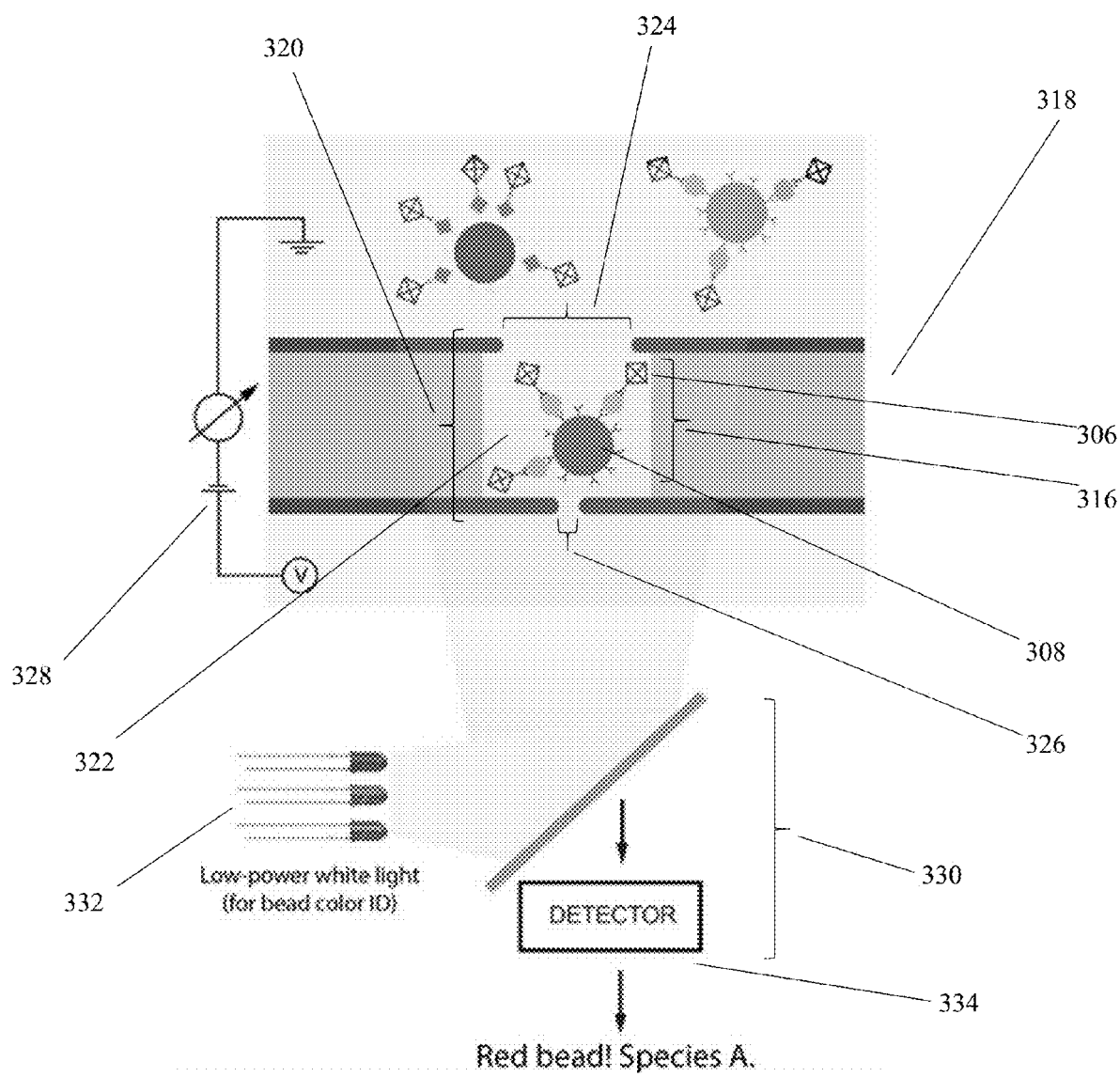
FIG. 3 is a schematic diagram illustrating capture of a species-loaded complex, and identifying the carrier particle, in accordance with an embodiment of the invention.

FIG. 3 is a schematic diagram illustrating capture of a species-loaded complex 316, and identifying the carrier particle 308, in accordance with an embodiment of the invention. In FIG. 3, the species-loaded complex 316 is captured in a portion of a device 318 to identify and quantify a species from a sample. The device 318 includes a microcavity structure 320 defining a microcavity 322. The microcavity structure 320 defines a first opening 324 of the microcavity 322 that is comparable in size to the carrier particle 308, to capture the species-loaded complex 316. By "comparable in size," in reference to the microcavity, it is meant that the microcavity is of a sufficiently close size to the carrier particle 308 that a single carrier particle 308 can enter the microcavity 322, but that not more than one of the carrier particle 308 can enter the microcavity 322 at once. In addition, it will be noted that the drawings are not to scale, and that typically, the components of the species-loaded complex 316 other than the carrier particle 308 itself will be of much smaller size than the carrier particle 308, so that the dimensions of the species-loaded complex 316 as a whole will be comparable to, and only slightly larger than, the carrier particle 308. The microcavity 322 can, for example, have a diameter of between about 2 microns and about 10 microns. The microcavity structure 320 further defines a second opening 326 of the microcavity 322 that is a nanopore 326, sized to have a comparable dimension to the nanoparticle 306 portion of the species-loaded complex 316, and to permit translocation of the nanoparticle 306. By "comparable dimension," in reference to the nanopore 326, it is meant that the nanopore 326 is sized so that the nanoparticle 306 is able to translocate through the nanopore 326, but temporarily occludes the nanopore 326 while it is translocating through the nanopore 326, to the extent that a temporary reduction in ionic current through the nanopore 326 can be detected, which is produced by the transient occlusion of the nanopore 326 by the nanoparticle 306 during the translocation of the nanoparticle 306 through the nanopore 326. For example, both the nanopore 326 and the nanoparticle 306 can have a diameter that is between about 1 nanometer and about 50 nanometers, with the nanoparticle 306 having a deformable quality so that it temporarily occludes the nanopore 326 but can translocate through the nanopore 326. The carrier particle 308, such as a bead, can be captured in the device 318 by applying a voltage across the device, for example using voltage source 328. A carrier particle detection component 330 is configured to, while the species-loaded complex 316 is captured, identify the carrier particle 308 based on its physical characteristics. The carrier particle detection component 330 can be configured to discriminate the carrier particle 308 optically, each of the plurality of different carrier particle types comprising an optical signature (such as a color, pattern, or other optical signature) corresponding uniquely to one of the plurality of different species in the sample. For example, a carrier particle 308 that is a bead can be identified optically, by its color, using white light from an illumination source 332, and a color detector 334. That permits distinguishing the type of the carrier particle 308 from amongst the multiple different carrier particle types; and, since each of the different carrier particle types correspond uniquely to one of the multiple different species in the sample, it allows identification 336 of the type of species 314 that is bound to the carrier particle 308. Although, here, the carrier particle detection component 330 is shown as including an illumination source 332 and color detector 334, it will be appreciated that other forms of carrier particle detection component 330 can be used. For example, carrier particles can be detected based on patterns formed on their surface, either optical or physical; or using electrical characteristics; or other physical characteristics. The carrier particle detection component 330, such as the color detector 334, can, for example, include one or more small Charge Coupled Device (CCD) cameras or Photomultiplier Tubes or Avalanche Photodetectors (PMTs or APDs) equipped with color filters, or a CMOS image sensor.

Figure 4:
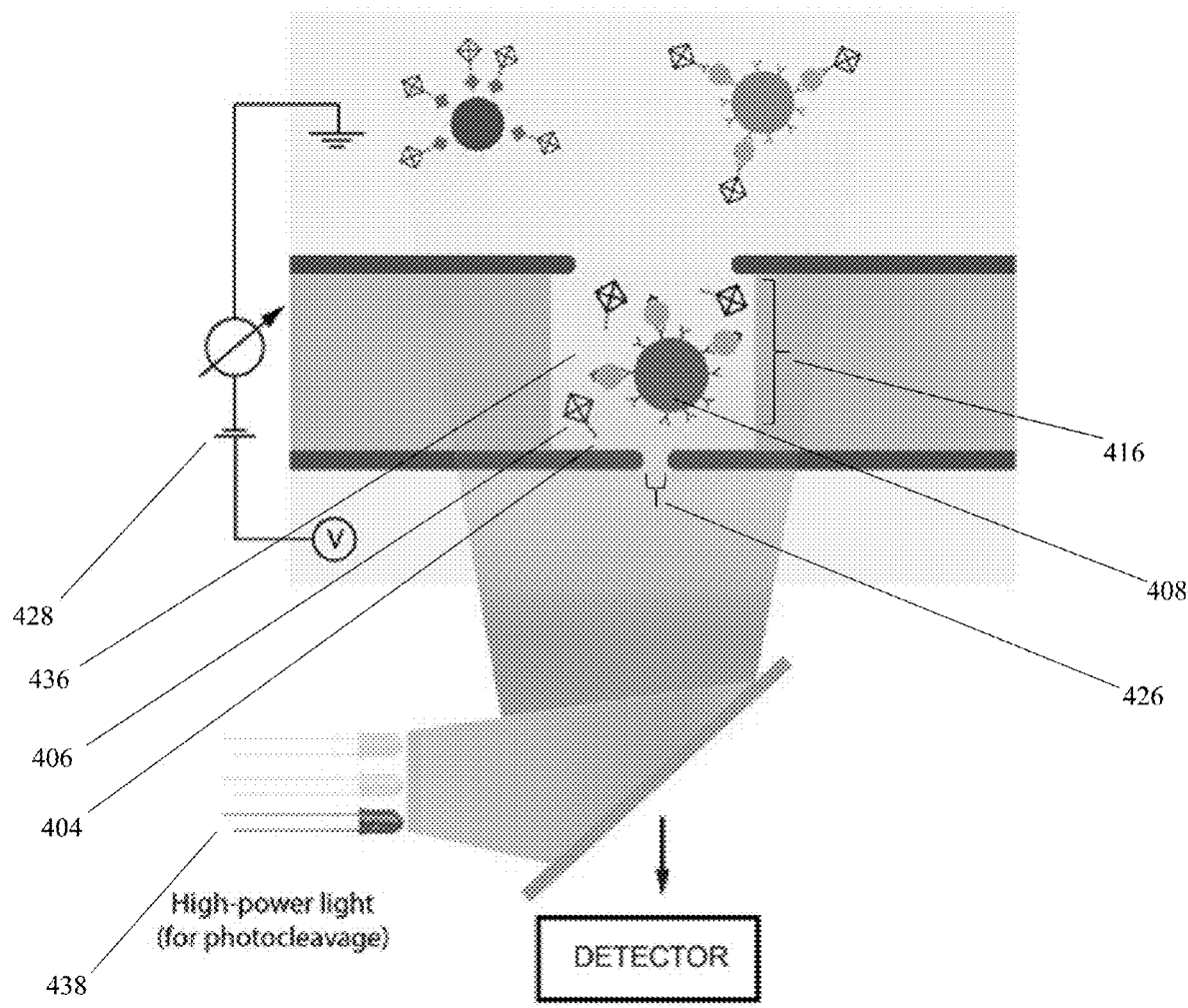
FIG. 4 is a schematic diagram illustrating cleaving of a species-loaded complex and release of a nanoparticle, in accordance with an embodiment of the invention.

FIG. 4 is a schematic diagram illustrating cleaving of a species-loaded complex 416 and release of a nanoparticle 406, in accordance with an embodiment of the invention. The voltage source 428 is configured to apply a voltage to an electrolyte 436 that surrounds the species-loaded complex 416, and which can, for example, fill or substantially fill the microcavity. The voltage is sufficient to translocate the nanoparticle 406 through the nanopore 426, once the nanoparticle 406 has been cleaved from the species-loaded complex 416. To perform the cleaving of the nanoparticle 406, upon having identified the carrier particle 408, as in FIG. 3, a cleaving component 438 is configured to cleave the cleavable linker 404 while the voltage is applied to the electrolyte 436 surrounding the species-loaded complex 416 by the voltage source 428. For example, where the cleavable linker 404 is a photocleavable linker, the cleaving component 438 can be a high-power, wavelength-specific illumination source (such as a light emitting diode, LED) that emits light of the specific wavelength to photocleave the cleavable linker 404, thereby releasing the nanoparticle 406 (such as an rNANP) from the species-loaded complex 416.

FIG. 5A is a schematic diagram illustrating nanoparticle counting and quantification, in accordance with an embodiment of the invention. FIG. 5B is a schematic diagram illustrating recording of ion flux as a function of time, produced by translocation of the nanoparticle through the nanopore, to permit the quantification, in accordance with an embodiment of the invention. Referring to FIG. 5A, the voltage source 528 applies a voltage that is sufficient to translocate the nanoparticle 506 through the nanopore 526. An electrical current processing circuit 540 is configured to detect an electrical current change produced as a result of the translocation of the nanoparticle 506 through the nanopore 526, thereby permitting quantification of the species. For example, referring to FIG. 5B, by measuring the electrical current changes, such as sudden current changes 542a and 542b, it is possible to count each time a nanoparticle 506 is translocated through the nanopore 526, where each current change 542a, 542b represents the translocation of a single nanoparticle 506 through the nanopore 526. Based on the total count of the nanoparticles 506, it is then possible to determine the concentration of the biomarker to which each of the nanoparticles 506 correspond. That is because, having identified the carrier particle, as in FIG. 3, and because the carrier particles correspond uniquely to the species-specific binders, it follows that the count of the nanoparticles 506 that are released when a given carrier particle is trapped, can be correlated with a count of the biomarkers bound to a given species to which each carrier particle corresponds through its having been coated with the species-specific binder. In one example, a nanoparticle 506 is an rNANP, and they are counted by recording the ion flux through the nanopore 526 as a function of time, either electrically or optically. The number of rNANPs detected can then be converted to the concentration of species in the original sample. After counting the nanoparticles released from each carrier particle that has been captured and identified, the carrier particle is released, and the process shown in FIGS. 3 through 5B is repeated to capture additional carrier particles and to detect different species bound to them. The process can be parallelized, using arrays of such microcavity-nanopore devices 318 to read multiple beads simultaneously.

In accordance with an embodiment of the invention, there is outlined next an example sequence of operation for a platform for biomarker detection.

A small sample of 1-2 μm carrier particles 208 (see FIG. 2) with an identifiable color is chemically treated so that the bead surfaces contain antibody A1, 210, which binds to biomarker A, 214a. The beads can, for example, be MicroPlex® microspheres, which are carboxylated polystyrene microparticles that are color coded into 100 spectrally distinct sets, and are sold by Luminex Corporation of Austin, Tex., U.S.A. The same process is repeated for other (different-color) beads to react them with antibody B1 (which binds to biomarker 214b), C1 (which binds to biomarker 214c), etc.

Once the beads are prepared, they are mixed together in a buffer solution 212. This solution is then exposed to a sample 214 on which diagnosis is needed (for example, saliva or serum from blood). This allows species 214a, 214b, 214c to bind to their designed target (e.g., specific antibodies) present on their respective beads 208a, 208b, 208c in the solution.

After beads are washed using a centrifugation/resuspension process, secondary antibodies 101 (see FIG. 1) are added to the biomarker. These antibodies bind to a second region of the biomarker, providing a "sandwich" 216 that is similar to an ELISA assay.

The secondary antibodies 101 (see FIG. 1) are chemically modified to have two features (all can be done using established protocols in biochemistry): 1) a photocleavable chemical group 104 at the tail of the antibody 101, and 2) A DNA oligo at that tail. This DNA oligo will be bound to a reporter nucleic acid nanoparticle (rNANP), 106. Design of such NANPs is, for example, achieved using open-source software (see http://daedalus-dna-origami.org, the entire disclosure of which is hereby incorporated herein by reference in its entirety), and the antibody 101 and photocleavable tag 104 are integrated into the tail of the nanoparticle 106.

Once prepared, these secondary antibodies 101 are exposed to the beads 208a, 208b, 208c (see FIG. 2), forming the sandwich 216. Remember: at the tail of the second antibody 101 that will now be on the bead only where a biomarker molecule is bound, there will be a rNANP, 206 (see FIG. 2), and a photocleavable molecule 204 that will release it to solution (see example chemistry here: Wegner, S. V. et al., "Photocleavable linker for the patterning of bioactive molecules," Scientific Reports, 5, Article No. 18309 (2015) https://www.nature.com/articles/srep18309, the entire disclosure of which is hereby incorporated herein by reference in its entirety.

Now the sample preparation steps are complete. For detection, see next step.

An open microfluidic channel that is, for example, approximately 10 μm wide and high will be formed on a glass cover slip. This will be bonded onto a silicon chip 318 (see FIG. 3) that contains a microcavity 322 that can host a single bead 308 at a time (say, for example, a cylindrical cavity of dimension about 2 μm) and a nanopore 326 at the bottom of this cavity.

The bonded device is used as a flow chamber to flow in beads, capture a bead 308 into the cavity 322, detect its color as in FIG. 3, and then release the rNANPs using a light pulse, as in FIG. 4.

Counting (see FIGS. 5A and 5B) the number of pulses from each bead that correspond to the rNANPs (as in the paper, Alibakhshi et al., "Picomolar Fingerprinting of Nucleic Acid Nanoparticles Using Solid-State Nanopores" ACS Nano, 11(10), 9701-9710, 2017 http://pubs.acs.org/ doi/10.1021/acsnano.7b04923, the entire disclosure of which is hereby incorporated herein by reference in its entirety) provides a digital count of the number of biomarkers on that bead, and knowing the color of that bead allows identification of that biomarker (because that was programmed into the chemistry). Each bead can carry on the order of $10^5$ molecules, affording a broad dynamic range.

Once a bead is consumed, it is ejected and flowed into a discarding reservoir.

The output of the measurement can be a biomarker panel that displays the "count" of each biomarker in the original sample.

Figures 6A, 6B, 6C, 6D, 6E, 6F, 6G:
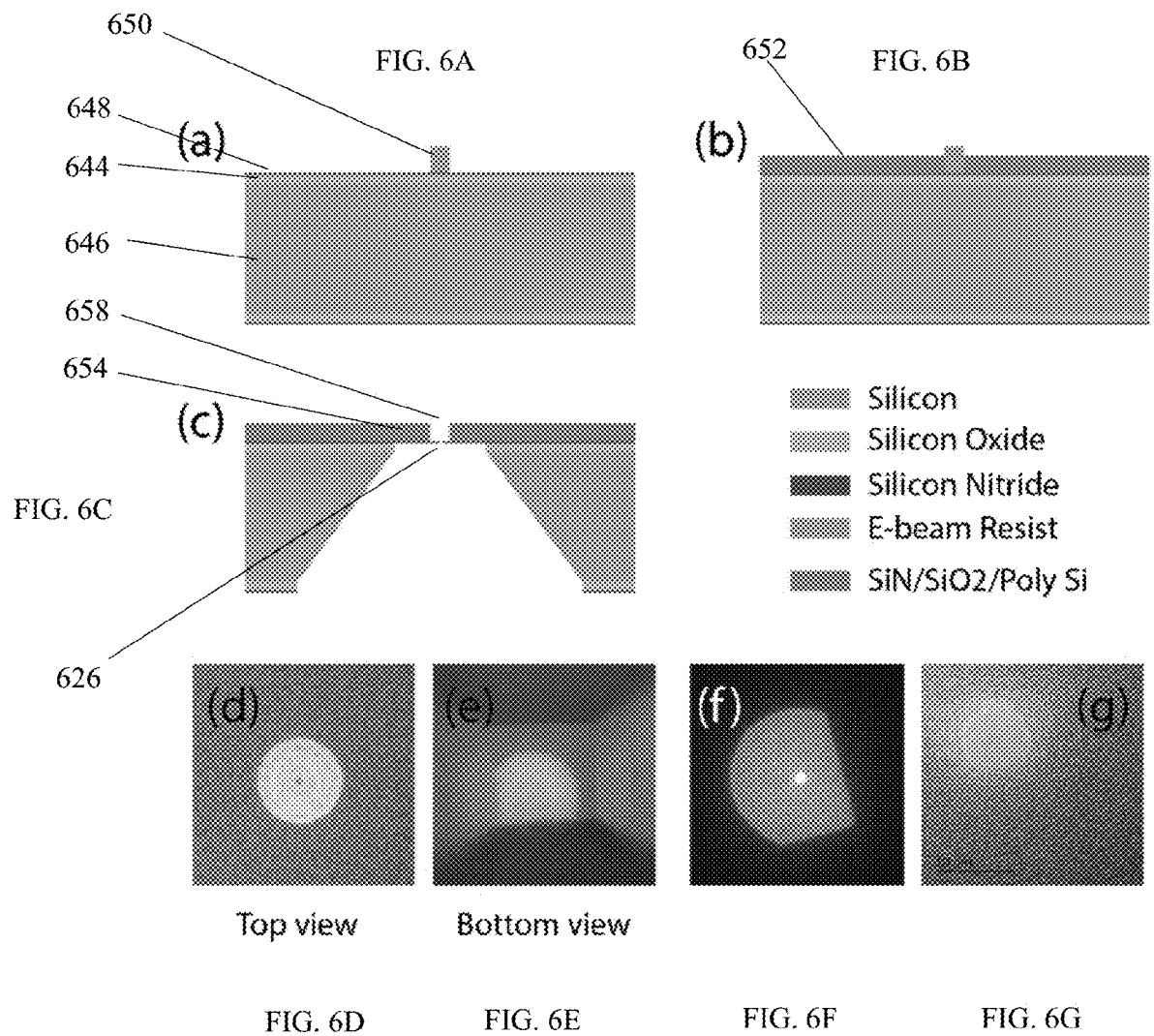
FIGS. 6A-6G are diagrams illustrating an example technique of fabrication of a microcavity-nanopore device, in accordance with an embodiment of the invention.

FIGS. 6A-6G are diagrams illustrating an example technique of fabrication of a microcavity-nanopore device, in accordance with an embodiment of the invention. In FIG. 6A, layers are created on a silicon wafer and a pillar is created by e-beam lithography or photolithography. A 2 micron thermal oxide layer 644 is grown on a 500-micron-thick silicon wafer 646. Next, 50 nm slow-stress LPCVD silicon nitride 648 is deposited on the wafer, followed by creation of a pillar 650, which can, for example be e-beam resist, and can, for example, be created by e-beam lithography or photolithography. In FIG. 6B, another layer 652 is deposited on the wafer, and can, for example, be a layer of silicon nitride, silicon oxide, or polysilicon. In FIG. 6C, resist lift-off is performed, a membrane 654 is created, as well as a microcavity 658, and a transmission electron microscope is used to drill a nanopore 626 in the membrane. FIG. 6D is a top view microscope image of the membrane; FIG. 6E is a bottom view image of the membrane; FIG. 6F shows a transmission electron micrograph image of the membrane; and FIG. 6G shows an image of the transmission electron microscope-drilled nanopore. It will be appreciated that a variety of other possible fabrication techniques can be used to create devices in accordance with an embodiment of the invention.

Figure 7:
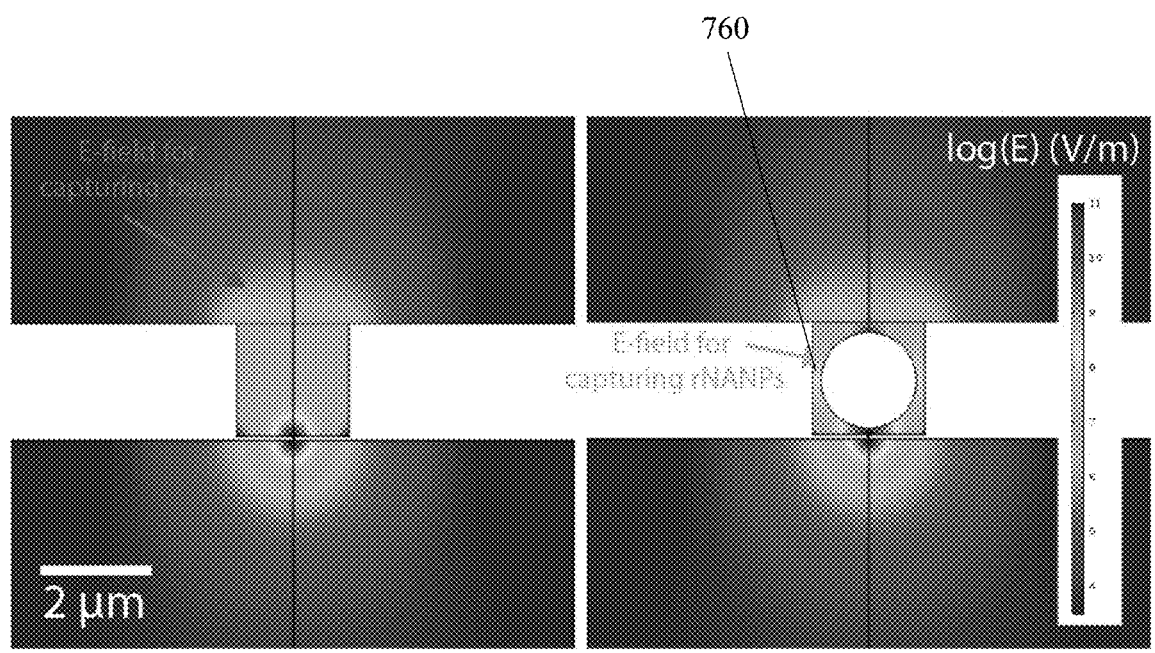
FIG. 7 is a diagram of results of an electrokinetic simulation of a microcavity-nanopore device, in accordance with an embodiment of the invention.

FIG. 7 is a diagram of results of an electrokinetic simulation of a microcavity-nanopore device, in accordance with an embodiment of the invention. On the left side is shown an electric field color plot in a 2-micron diameter microcavity-nanopore device ($d_{pore}$=15 nm, V=1 volt, in 400 mM KCl. On the right side is shown the same simulation as the left image, after placement of a 1.7 µm bead in the microcavity. The residual electric field 760 within the cavity is strong enough to prevent escape of the nanoparticle, such as an rNANP, thereby allowing quantitative capture of the released nanoparticles from the bead.

Figure 8:
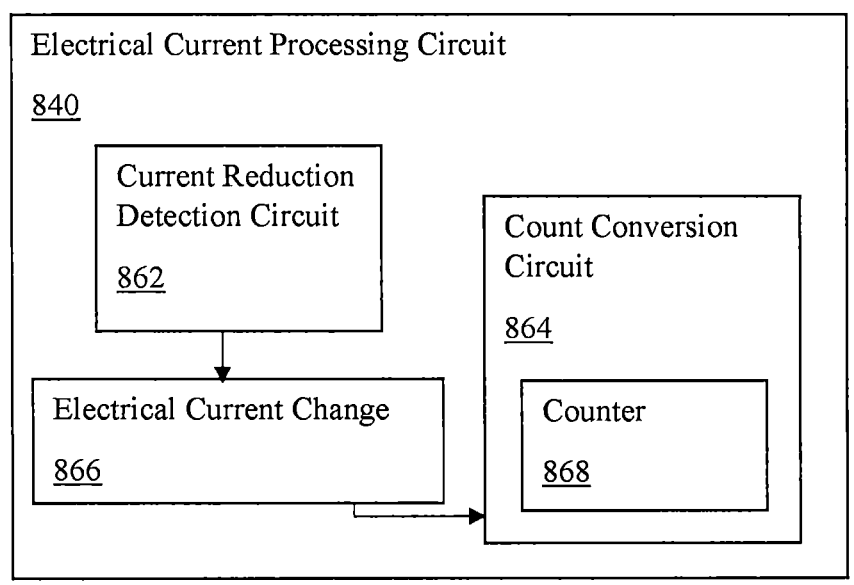
FIG. 8 is a schematic diagram of an electrical current processing circuit, in accordance with an embodiment of the invention.

FIG. 8 is a schematic diagram of an electrical current processing circuit 840, in accordance with an embodiment of the invention. The electrical current processing circuit 840 can, for example, be the electrical current processing circuit 540 of FIG. 5. In FIG. 8, the electrical current processing circuit 840 includes a current reduction detection circuit 862, which detects a temporary reduction in ionic current through the nanopore (such as 542a, 542b of FIG. 5B) produced by transient occlusion of the nanopore by the nanoparticle during the translocation of the nanoparticle through the nanopore produced by the applying the voltage of the voltage source 528 (see FIG. 5A). The electrical current processing circuit 840 (see FIG. 8) also includes a count conversion circuit 864, which electrically translates the electrical current change 866, output from the current reduction detection circuit 862, to an electrical signal representing an integer counting of the species, for example, by incrementing a counter 868 each time the electrical current change exceeds a threshold. The circuit 840 can base its detection on the magnitude of the drop in current, and its duration. Generally, each drop in current corresponds to a single nanoparticle being translocated through the nanopore. Further background on types of electrical signal processing that can, for example, be used are in the paper, Alibakhshi et al., "Picomolar Fingerprinting of Nucleic Acid Nanoparticles Using Solid-State Nanopores" ACS Nano, 11(10), 9701-9710, 2017 https://pubs.acs.org/doi/10.1021/acsnano.7b04923, the entire disclosure of which is hereby incorporated herein by reference in its entirety. The count conversion circuit 864 can, for example, perform computations related to the amount of the species in the sample, or can perform calculations based on known standards.

Figure 9:
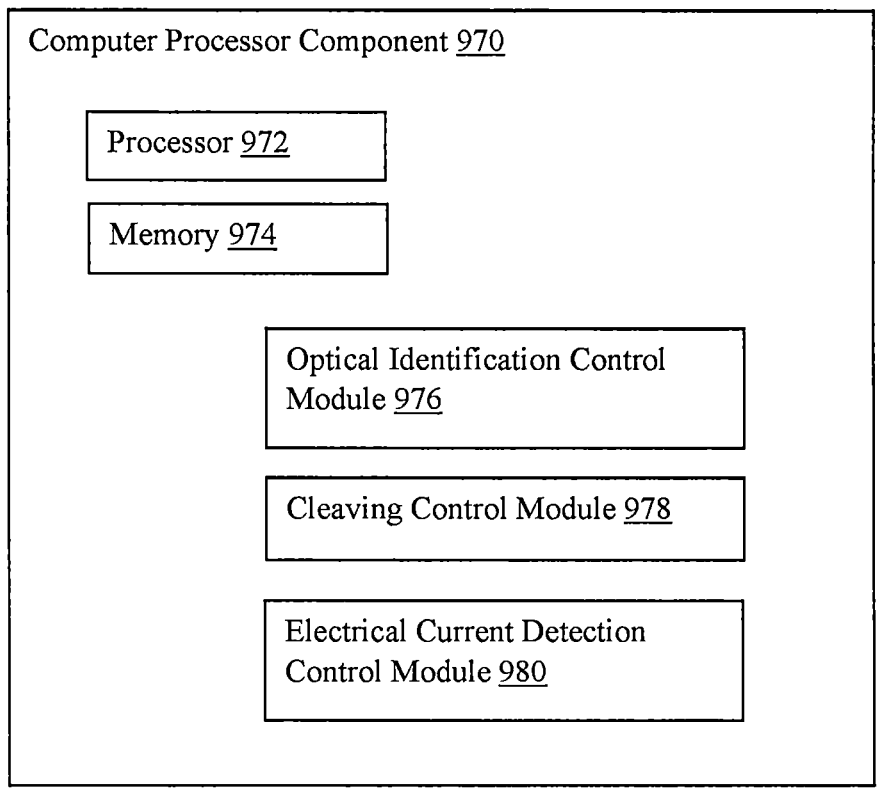
FIG. 9 is a schematic diagram of a computer processor component that can be included in a device in accordance with an embodiment of the invention.

FIG. 9 is a schematic diagram of a computer processor component 970 that can be included in a device in accordance with an embodiment of the invention. The computer processor component 970 includes a processor 972, and a memory 974 with computer code instructions stored thereon. The processor 972 and the memory 974, with the computer code instructions are configured to implement three modules, which, it will be appreciated, can be implemented as one or more sub-modules of a single or multiple processing units. A first module is an optical identification control module 976 configured to, following the capturing of the species-loaded complex 316 (see FIG. 3), control an optical component (such as illumination source 332) and an electrical signal processing component (such as color detector 334) to identify the carrier particle 308 (see FIG. 3) based on its physical characteristics. A second module is a cleaving control module 978 configured to, following the identification of the carrier particle 416 (see FIG. 4), control a cleaving component (such as 438) to cleave the cleavable linker (404). A third module is an electrical current detection control module 980 configured to control current detection circuitry (such as 540, see FIG. 5A) to detect the electrical current change (such as 542a, 542b of FIG. 5B) produced as a result of the translocation of the nanoparticle through the nanopore. It will be appreciated that each of the components of the computer processor component 970 can be connected by appropriate signal processing lines, not shown, to the various components that they control. In addition, it will be appreciated that, although several components discussed herein are shown in separate diagrams, they can be joined together in appropriate operative combinations as needed to implement embodiments taught herein.

Figure 10:
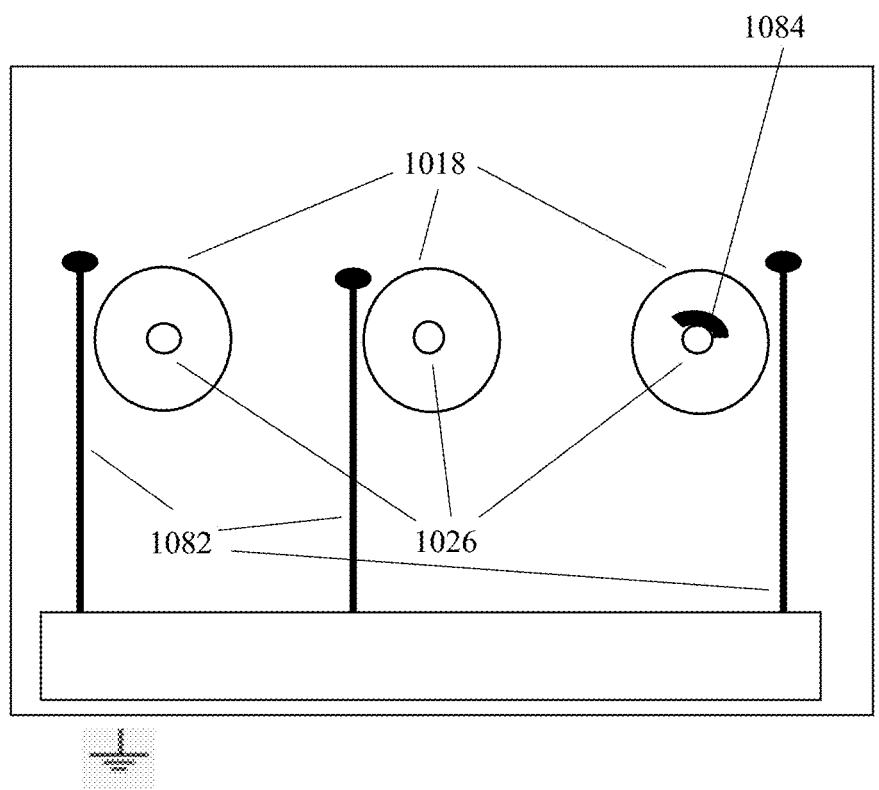
FIG. 10 is a schematic diagram of a device that includes multiple microcavity structures, in accordance with an embodiment of the invention.

FIG. 10 is a schematic diagram of a device that includes multiple microcavity structures 1018, in accordance with an embodiment of the invention. Each microcavity structure 1018 defines a second opening of each microcavity that is a nanopore 1026, sized to have a comparable dimension to the nanoparticle and to permit translocation of the nanoparticle. The method can be performed for multiple different species in the same sample simultaneously, using the multiple nanopores 1026 of the device. The device can include multiple electrodes 1082, with each electrode corresponding to a single nanopore 1026. The method can include applying the voltage to the electrolyte 436 (see FIG. 4) surrounding the species-loaded complex, using the multiple electrodes 1082, each electrode corresponding to a single nanopore 1026. In one embodiment, the device 1018 includes an electrode 1018, in electrical connection with the nanopore 1026, that is configured to cleave the cleavable linker 404 (see FIG. 4). For example, in this embodiment, the cleavable linker 404 can be one that is cleaved based on a pH of the electrolyte surrounding the cleavable linker 404, and the pH can be changed by applying a voltage to the electrode 1018, such as a platinum electrode. In another embodiment, the electrode 1084 can be formed of at least part of the microcavity structure that defines the nanopore 1026 of the microcavity, for example by defining at least part of the wall of the nanopore as at 1084 in FIG. 10. Electrodes 1018 can permit individual addressing of each microcavity structure.

In another embodiment according to the invention, there is provided a kit for identifying and quantifying a species from a sample. The kit comprises a plurality of different carrier particle types, each of the plurality of different carrier particle types corresponding uniquely to one of a plurality of different species in the sample. For each of the plurality of different species in the sample, the kit comprises a first species-specific binder, to specifically bind the species to the carrier particle to which it uniquely corresponds. For each of the plurality of different species in the sample, the kit comprises a nanoparticle complex comprising: (i) a second species-specific binder, to bind specifically to the species, (ii) a nanoparticle, and (iii) a cleavable linker, linking the second species-specific binder to the nanoparticle.

In accordance with an embodiment of the invention, some example aspects of the technology are: 1) that it integrates single-entity counting with bead ID technology to enable multiplexed sensing of different species; 2) that detection involves deformable programmable nucleic-acid-based geometrical sensors, which enable pM-level detection and an enormous five, six or more orders of magnitude dynamic range; 3) that photocleavage of species from the bead enables their efficient release into the sensor; and 4) that capture of species into the detector is facilitated by high electric fields that are geometrically controlled by the sensor shape, ensuring detection. Detection of sub-picomolar level species is not commercially available currently, and extremely difficult to achieve. Furthermore, the multiplexing approach, in combination with nanopore (true single molecule) detection, affords portability and reliability. Embodiments permit targeting of cancers by early detection, through detection of small protein amounts in large volumes. Also, neonatal diseases can be targeted that require answers from small sample amounts. Sepsis can also be targeted. Multiplexing can be performed in a small size, as compared with other types of multiplexing, which require large formats and accompanying sensors (such as 96-well plates). Illumination/photocleavage can be performed using LEDs, and sensing using small CCD cameras or PMTs/APDs equipped with color filters. In addition, the platform can be fast, and can display real-time counting data as the detection takes place.

As used herein, a "species-specific binder" is a binder that binds to a species, such as a molecular species, in a sample, with negligible or no binding to other species present in the sample, under a given set of binding conditions. For example, the species-specific binder can be or include at least one of: a protein, a nucleic acid, a polymer and a chelating agent. In further examples, the species-specific binder can be or include at least one of: deoxyribonucleic acid (DNA), ribonucleic acid (RNA), a polymer, an antibody, an aptamer, a single-stranded nucleic acid, a Clustered Regularly Interspaced Short Palindromic Repeats (CRISPR) nucleic acid guide, and a polyhistidine tag. The two different species-specific binders used (such as binders 101 and 210) can be a pair of antibodies, each of the antibodies binding to different epitopes of the same species. The antibodies can be whole antibodies or antibody fragments (e.g., a single-chain Fv fragment or Fab antibody fragment), provided that the antibody or antibody fragment is able to recognize and bind to its specific species. Examples of antigen-binding fragments of an antibody include, e.g., a Fab, Fab', F(ab')2, Fv, scFv, dsFv, dAb, and a diabody. The species-specific binder can be a linker polymer, wherein the linker polymer is a heteropolymer. A heteropolymer is a polymer derived from at least two different types of monomer.

As used herein, a "species" can, for example, be or include at least one of: a nucleic acid molecule (for example, deoxyribonucleic acid, DNA, or ribonucleic acid, RNA), a protein, a cell, a bacteria, a virus, a fungus, a polypeptide, a polysaccharide and an organic drug. For example, the species can be or include microRNA, DNA, or a blood factor. The species can be or include at least a portion of at least one of: a biomarker, a circulating tumor cell nucleic acid, a circulating tumor protein, a circulating tumor cell, and a white blood cell. The species can be at least one of: a prostate-specific antigen; thrombin; an indicator of metastatic cancer; a fetal nucleic acid; a fetal protein. An organic drug is a drug, vaccine or antitoxin that is made from a living organism, or from products of a living organism.

As used herein, a "sample" can include any biological or organic sample suitable for analysis using techniques taught herein, including, for example, serum (e.g., clinical serum), saliva or a blood sample. Other suitable samples include, but are not limited to, blood, lymph fluid, bone marrow, or any combination. In one embodiment, the sample can be a maternal blood sample, and the species can include at least one of a fetal nucleic acid and a fetal protein.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A method of identifying and quantifying a species from a sample, the method comprising:
   capturing a species-loaded complex, the species-loaded complex comprising: (i) the species, isolated from the sample, (ii) a carrier particle, (iii) a first species-specific binder, binding the species to the carrier particle, (iv) a second species-specific binder, bound to the species, (v) a nanoparticle, and (vi) a cleavable linker, linking the second species-specific binder to the nanoparticle;
   while the species-loaded complex is captured, identifying the carrier particle based on its physical characteristics, thereby permitting distinguishing a type of the carrier particle from amongst a plurality of different carrier particle types, each of the plurality of different carrier particle types corresponding uniquely to one of a plurality of different species in the sample;
   upon having identified the carrier particle, cleaving the cleavable linker while applying a voltage to an electrolyte surrounding the species-loaded complex, the voltage being sufficient to translocate the nanoparticle through a nanopore; and
   detecting an electrical current change produced as a result of the translocation of the nanoparticle through the nanopore, thereby permitting quantification of the species.

2. The method of claim 1, wherein capturing the species-loaded complex comprises capturing the species-loaded complex within a microcavity structure defining a microcavity, the species-loaded complex being captured within the microcavity, the microcavity structure defining a first opening of the microcavity comparable in size to the carrier particle, and the microcavity structure defining a second opening of the microcavity that is a nanopore, sized to have a comparable dimension to the nanoparticle and to permit translocation of the nanoparticle.

3. The method of claim 2, wherein the microcavity has a diameter of between about 2 microns and about 10 microns.

4. The method of claim 3, wherein the nanopore has a diameter of between about 1 nanometer and about 50 nanometers.

5. The method of claim 1, wherein the nanoparticle comprises a deformable reporter nucleic acid nanoparticle.

6. The method of claim 5, wherein detecting the electrical current change comprises detecting a temporary reduction in ionic current through the nanopore produced by transient occlusion of the nanopore by the nanoparticle during the translocation of the nanoparticle through the nanopore produced by the applying the voltage.

7. The method of claim 1, further comprising electrically translating the electrical current change to an electrical signal representing an integer counting of the species.

8. The method of claim 1, wherein the cleavable linker comprises at least one of a photocleavable linker and a chemically-cleavable linker.

9. The method of claim 8, wherein the cleavable linker comprises a photocleavable linker, and cleaving the cleavable linker comprises illuminating the photocleavable linker with light of a wavelength specific to cleaving of the photocleavable linker.

10. The method of claim 1, wherein identifying the carrier particle based on its physical characteristics comprises optically discriminating the carrier particle, each of the plurality of different carrier particle types comprising an optical signature corresponding uniquely to one of the plurality of different species in the sample.

11. The method of claim 1, wherein the carrier particle comprises a bead having a diameter between about 2 microns and about 10 microns.

12. The method of claim 1, wherein the first species-specific binder and the second species-specific binder comprise a pair of antibodies, each of the antibodies binding to different epitopes of the same species.

13. The method of claim 1, wherein the species comprises at least a portion of at least one of: a biomarker, a circulating tumor cell nucleic acid, a circulating tumor protein, a circulating tumor cell, and a white blood cell.

14. The method of claim 13, wherein the species comprises at least one of: a prostate-specific antigen; thrombin; an indicator of metastatic cancer; a fetal nucleic acid; a fetal protein.

* * * * *